United States Patent
Colson et al.

(10) Patent No.: US 8,658,691 B2
(45) Date of Patent: Feb. 25, 2014

(54) CRYSTALLINE FORMS OF A 3-[2-METHANESULFONYL-1-(4-TRIFLUOROMETHYL-PHENOXY)ETHYL] PYRROLIDINE COMPOUND

(71) Applicants: Pierre-Jean Colson, San Francisco, CA (US); Timothy Fass, San Francisco, CA (US); Venkat R. Thalladi, Foster City, CA (US)

(72) Inventors: Pierre-Jean Colson, San Francisco, CA (US); Timothy Fass, San Francisco, CA (US); Venkat R. Thalladi, Foster City, CA (US)

(73) Assignee: Theravance, Inc., South San Francisco, CA (US)

( * ) Notice: Subject to any disclaimer, the term of this patent is extended or adjusted under 35 U.S.C. 154(b) by 0 days.

(21) Appl. No.: 13/630,992

(22) Filed: Sep. 28, 2012

(65) Prior Publication Data

US 2013/0085172 A1    Apr. 4, 2013

Related U.S. Application Data

(60) Provisional application No. 61/541,277, filed on Sep. 30, 2011.

(51) Int. Cl.
*A01N 43/36* (2006.01)
*A61K 31/40* (2006.01)
*C07D 207/46* (2006.01)
*C07D 295/00* (2006.01)

(52) U.S. Cl.
USPC ............................. 514/428; 514/708; 548/570

(58) Field of Classification Search
None
See application file for complete search history.

(56) References Cited

U.S. PATENT DOCUMENTS

2008/0228012 A1* 9/2008 Ino et al. .................. 568/700
2012/0088799 A1* 4/2012 Stangeland et al. .......... 514/343

FOREIGN PATENT DOCUMENTS

WO        2011/011231 A1    1/2011

OTHER PUBLICATIONS

International Search Report for PCT Application PCT/US2012/057990 dated Nov. 19, 2012.

* cited by examiner

*Primary Examiner* — Craig Ricci
*Assistant Examiner* — Jared D Barsky
(74) *Attorney, Agent, or Firm* — Jeffrey A. Hagenah; Shelley Eberle

(57) ABSTRACT

The invention provides crystalline hydrochloride salts of (S)-3-[(S)-2-methanesulfonyl-1-(4-trifluoromethylphenoxy) ethyl]pyrrolidine. This invention also provides pharmaceutical compositions comprising the crystalline salts, processes and intermediates for preparing the crystalline salts, and methods of using the crystalline salts to treat diseases.

3 Claims, 9 Drawing Sheets

CRYSTALLINE FORMS OF A 3-[2-METHANESULFONYL-1-(4-TRIFLUOROMETHYL-PHENOXY)ETHYL] PYRROLIDINE COMPOUND

CROSS-REFERENCE TO RELATED APPLICATIONS

This application claims the benefit of U.S. Provisional Application No. 61/541,277, filed on Sep. 30, 2011; the entire disclosure of which is incorporated herein by reference.

BACKGROUND OF THE INVENTION

1. Field of the Invention

The present invention relates to novel crystalline forms of a 3-(sulfonyl-1-phenoxyethyl)pyrrolidine compound, which has activity as a serotonin (5-HT) reuptake inhibitor and, in one embodiment, has the characteristic of being selectively restricted from the central nervous system.. The invention also relates to pharmaceutical compositions comprising such compounds, processes, and intermediates for preparing such compounds and methods of using such compounds to treat pulmonary arterial hypertension and other ailments.

2. State of the Art

U.S. Patent Application Publication No. 2012/0088799 to Stangeland et al. discloses novel compounds that have activity as a serotonin (5-HT) reuptake inhibitors, the disclosure of which is incorporated herein by reference. In particular, the compound, (S)-3-[(S)-2-methanesulfonyl-1-(4-trifluoromethyl-phenoxy)ethyl]pyrrolidine is specifically disclosed in this application.

The chemical structure of (S)-3-[(S)-2-methanesulfonyl-1-(4-trifluoromethyl-phenoxy)ethyl]pyrrolidine is represented by formula I:

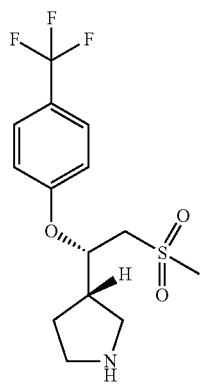

(I)

When preparing compounds for long term storage and when preparing pharmaceutical compositions and formulations, it is often desirable to have a crystalline form of the therapeutic agent that is neither hygroscopic nor deliquescent. It is also advantageous to have a crystalline form that has a relatively high melting point (i.e. greater than about 150° C.), which allows the material to be processed, for example, micronized, without significant decomposition. Accordingly, a need exists for a stable, non-deliquescent form of (S)-3-[(S)-2-methanesulfonyl-1-(4-trifluoromethylphenoxy) ethyl]-pyrrolidine which has an acceptable level of hygroscopicity and a relatively high melting point.

SUMMARY OF THE INVENTION

One aspect of the invention relates to a crystalline hydrochloride salt of (S)-3-[(S)-2-methanesulfonyl-1-(4-trifluoromethylphenoxy)ethyl]pyrrolidine, selected from: (a) an anhydrous Form I, characterized by a powder x-ray diffraction pattern comprising diffraction peaks at 2θ values of 5.37±0.20, 9.89±0.20, 10.28±0.20, 16.06±0.20, 16.66±0.20, 19.90±0.20, 21.46±0.20, 23.18±0.20, 26.88±0.20, and 27.28±0.20; (b) an anhydrous Form II, characterized by a powder x-ray diffraction pattern comprising diffraction peaks at 2θ values of 7.14±0.20, 9.86±0.20, 11.38±0.20, 14.20±0.20, 15.64±0.20, 18.00±0.20, 21.38±0.20, 22.24±0.20, 30.20±0.20, and 36.36±0.20; and (c) a monohydrate, characterized by a powder x-ray diffraction pattern comprising diffraction peaks at 2θ values of 11.54±0.20, 14.38±0.20, 14.96±0.20, 16.44±0.20, 18.30±0.20, 19.62±0.20, 21.56±0.20, 24.56±0.20, 25.06±0.20, 25.96±0.20, and 26.92±0.20.

Another aspect of the invention relates to processes for preparing crystalline hydrochloride salt forms of (S)-3-[(S)-2-methanesulfonyl-1-(4-trifluoromethylphenoxy)-ethyl]pyrrolidine. In one embodiment, a process for preparing a crystalline hydrochloride anhydrous Form I salt of (S)-3-[(S)-2-methanesulfonyl-1-(4-trifluoromethylphenoxy)-ethyl] pyrrolidine comprises the steps of: (a) treating a hydrochloride salt of (S)-3-[(S)-2-methanesulfonyl-1-(4-trifluoromethylphenoxy)-ethyl]pyrrolidine with cyclopentyl methyl ether or deprotecting (S)-3-[(S)-2-methanesulfonyl-1-(4-trifluoromethylphenoxy)-ethyl]pyrrolidine-1-carboxylic acid t-butyl ester with hydrochloric acid in cyclopentyl methyl ether; and (b) isolating the resulting solids to yield the crystalline hydrochloride anhydrous Form I salt. In one embodiment, a process for preparing a crystalline hydrochloride anhydrous Form II salt of (S)-3-[(S)-2-methanesulfonyl-1-(4-trifluoromethylphenoxy)ethyl]pyrrolidine comprises the steps of: (a) treating a hydrochloride salt of (S)-3-[(S)-2-methanesulfonyl-1-(4-trifluoromethylphenoxy)-ethyl]pyrrolidine with cyclopentyl methyl ether and water; and (b) isolating the resulting solids to yield the crystalline hydrochloride anhydrous Form II salt. In one embodiment, a process for preparing a crystalline hydrochloride monohydrate salt of (S)-3-[(S)-2-methanesulfonyl-1-(4-trifluoromethylphenoxy)ethyl]pyrrolidine comprises the steps of: (a) exposing a crystalline hydrochloride salt Form I of (S)-3-[(S)-2-methanesulfonyl-1-(4-trifluoromethylphenoxy)ethyl]pyrrolidine to moisture; and (b) isolating the resulting solids to yield the crystalline hydrochloride monohydrate salt.

Another aspect of the invention relates to a process for purifying (S)-3-[(S)-2-methanesulfonyl-1-(4-trifluoromethylphenoxy)ethyl]pyrrolidine. In one embodiment, this process comprises forming a crystalline hydrochloride salt of (S)-3-[(S)-2-methanesulfonyl-1-(4-trifluoromethylphenoxy) ethyl]pyrrolidine. The invention also relates to products prepared by the processes described herein. In specific embodiments, the crystalline hydrochloride salt is anhydrous Form I, anhydrous Form II, or a monohydrate.

One aspect of the invention relates to a pharmaceutical composition comprising a pharmaceutically acceptable carrier and a crystalline hydrochloride salt of (S)-3-[(S)-2-methanesulfonyl-1-(4-trifluoromethylphenoxy)ethyl]pyrrolidine. In specific embodiments, the crystalline hydrochloride salt is anhydrous Form I, anhydrous Form II, or a monohydrate. Such compositions may optionally contain other active agents such as calcium channel blockers, endothelin receptor antagonists, PDE-5 inhibitors, prostacycline analogues, prostanoids, and combinations thereof Accordingly, in yet another aspect of the invention, a pharmaceutical composition comprises the crystalline salt of the invention, a second active agent, and a pharmaceutically acceptable carrier. Another aspect of the invention relates to a combination of active agents, comprising the crystalline salt of the invention and a second active agent. The crystalline salt of the invention can be formulated together or separately from the additional agent(s). When formulated separately, a pharmaceutically acceptable carrier may be included with the additional agent(s). Thus, yet another aspect of the invention relates to a combination of pharmaceutical compositions, the combination comprising: a first pharmaceutical composition comprising the crystalline salt of the invention and a first pharmaceutically acceptable carrier; and a second pharmaceutical composition comprising a second active agent and a second pharmaceutically acceptable carrier. The invention also relates to a kit containing such pharmaceutical compositions, for example where the first and second pharmaceutical compositions are separate pharmaceutical compositions.

(S)-3-[(S)-2-methanesulfonyl-1-(4-trifluoromethylphenoxy)ethyl]pyrrolidine possesses serotonin reuptake inhibition activity. The crystalline hydrochloride salts of this compound are expected to be useful as a therapeutic agent for treating patients suffering from a disease or disorder that is treated by the inhibition of the serotonin transporter primarily in the periphery as compared to the CNS. Thus, one aspect of the invention relates to a method of treating a disease selected from pulmonary arterial hypertension, gastrointestinal disorders, cancer, rheumatoid arthritis, osteoarthritis, osteoporosis, and diabetes, comprising administering to a patient a therapeutically effective amount of a compound of the invention. In one specific aspect, the invention relates to a method of treating pulmonary arterial hypertension. Another aspect of the invention relates to a method of treating a patient that is in need of anti-platelet therapy, comprising administering to a patient a therapeutically effective amount of a crystalline compound of the invention.

Yet another aspect of the invention relates to the use of the crystalline compounds of the invention for the manufacture of medicaments, especially for the manufacture of medicaments useful for treating pulmonary arterial hypertension, for anti-platelet therapy, or for inhibiting serotonin reuptake in a mammal Still another aspect of the invention relates to the use of the crystalline compounds of the invention as research tools. Other aspects and embodiments of the invention are disclosed herein.

BRIEF DESCRIPTION OF THE DRAWINGS

Various aspects of the present invention are illustrated by reference to the accompanying drawings.

DETAILED DESCRIPTION OF THE INVENTION

Figure 1:
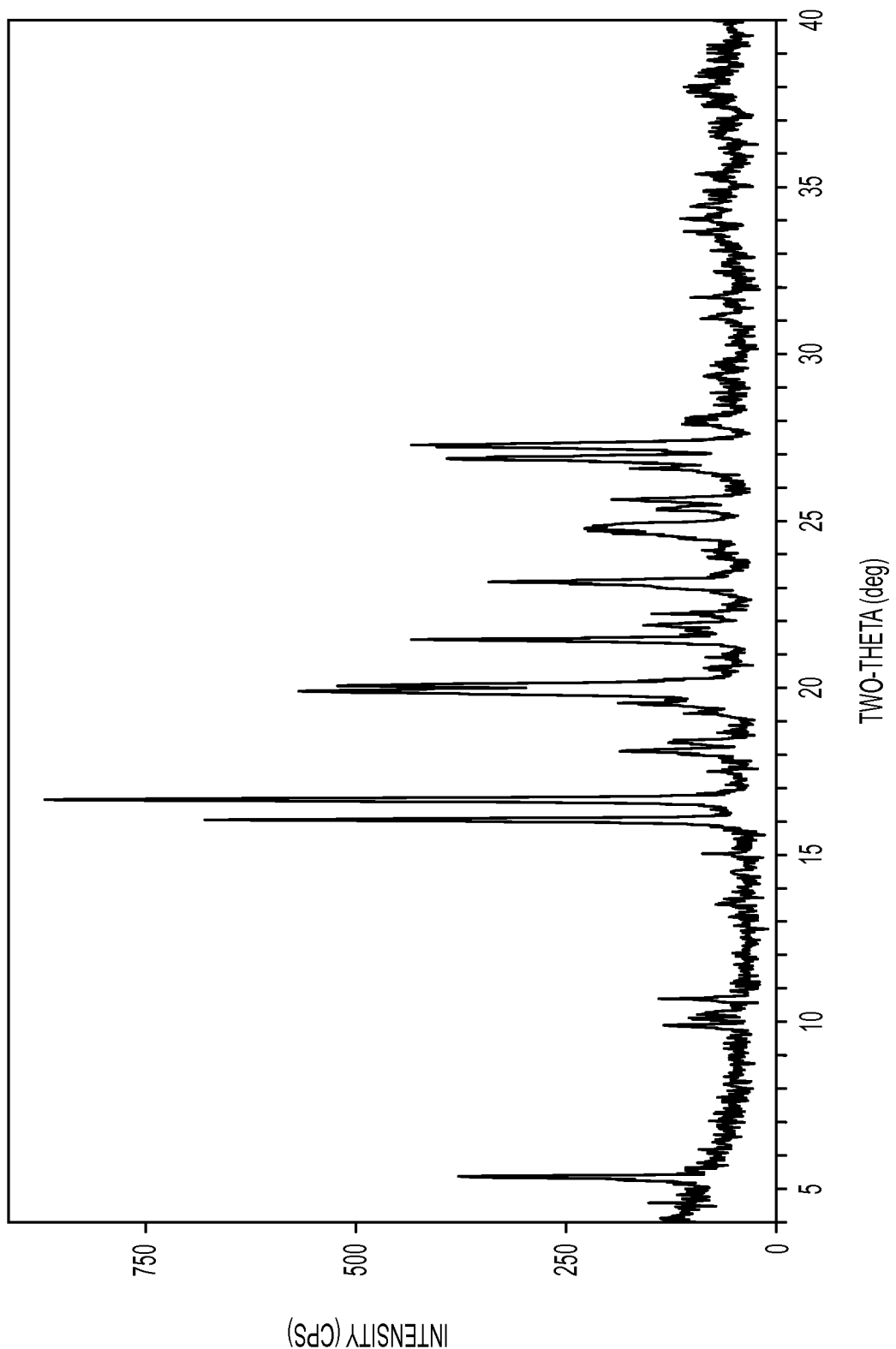
FIG. 1 shows a powder x-ray diffraction (PXRD) pattern of the crystalline hydrochloride anhydrous Form I salt of (S)-3-[(S)-2-methanesulfonyl-1-(4-trifluoromethylphenoxy)ethyl]pyrrolidine.

This invention provides crystalline hydrochloride salts of (S)-3-[(S)-2-methanesulfonyl-1-(4-trifluoromethylphenoxy)ethyl]pyrrolidine. The active agent (i.e., the compound of formula I) contains two chiral centers having the (S,S) configuration. However, it will be understood by those skilled in the art that minor amounts of the (S,R), (R,S), and/or (R,R) stereoisomers may be present in the compositions of the invention unless otherwise indicated, provided that the utility of the composition as a whole is not eliminated by the presence of such stereoisomers.

The compound of formula I has activity as a serotonin (5-HT) reuptake inhibitor. Crystalline forms of the compound of formula I are expected to have the same activity, and thus the same utility in treating diseases such as pulmonary arterial hypertension or for treating patients in need of anti-platelet therapy. Therefore, among other uses, the crystalline forms of the invention are useful for preparing pharmaceutical compositions for treating such diseases.

DEFINITIONS

When describing the compounds, compositions, methods and processes of the invention, the following terms have the following meanings unless otherwise indicated.

Additionally, as used herein, the singular forms "a," "an" and "the" include the corresponding plural forms unless the context of use clearly dictates otherwise. The terms "comprising", "including," and "having" are intended to be inclusive and mean that there may be additional elements other than the listed elements. All numbers expressing quantities of ingredients, properties such as molecular weight, reaction conditions, and so forth used herein are to be understood as being modified in all instances by the term "about," unless otherwise indicated. Accordingly, the numbers set forth herein are approximations that may vary depending upon the desired properties sought to be obtained by the present invention. At least, and not as an attempt to limit the application of the doctrine of equivalents to the scope of the claims, each number should at least be construed in light of the reported significant digits and by applying ordinary rounding techniques.

As used herein, the phrase "of the formula", "having the formula" or "having the structure" is not intended to be limiting and is used in the same way that the term "comprising" is commonly used.

The crystalline hydrochloride salt anhydrous Form I and anhydrous Form II are monohydrochloride salts. The term "mono" as used herein is intended to mean that the crystalline form typically contains about 1.0 molar equivalents of freebase (the compound of formula I) per about 1.0±0.15 molar equivalent of counterion; and in one embodiment, about 1.0 molar equivalents of freebase per about 1.0 molar equivalent of counterion. Thus, the crystalline hydrochloride salts generally contain about 1.0 molar equivalents of freebase per about 1.0±0.15 molar equivalent of hydrochloric acid; and in one embodiment, about 1.0 molar equivalents of freebase per about 1.0 molar equivalent hydrochloric acid.

The term "hydrate" means a crystal form, where molecules of water are incorporated in the unit cell of the crystal lattice. The hydrate may include one or more molecules of water, but the number of water molecules may also be a fraction of one, such as one-half or one-fourth. In the present invention, the hydrate form is a monohydrochloride monohydrate and generally contains about 1.0 molar equivalents of freebase per about 1.0±0.15 molar equivalents of hydrochloric acid and about 1.0±0.15 molar equivalents of water; and in one embodiment, about 1.0 molar equivalents of freebase per about 1.0 molar equivalent of hydrochloric acid and about 1.0 molar equivalent of water.

The term "melting point" or "melting endotherm" as used herein means the temperature at which the maximum endothermic heat flow is observed by differential scanning calorimetry, for the thermal transition that corresponds to the solid-to-liquid phase change.

The term "pharmaceutically acceptable" refers to a material that is not biologically or otherwise unacceptable when used in the invention. For example, the term "pharmaceutically acceptable carrier" refers to a material that can be incorporated into a composition and administered to a patient without causing unacceptable biological effects or interacting in an unacceptable manner with other components of the composition. Such pharmaceutically acceptable materials typically have met the required standards of toxicological and manufacturing testing, and include those materials identified as suitable inactive ingredients by the U.S. Food and Drug Administration.

The term "therapeutically effective amount" means an amount sufficient to effect treatment when administered to a patient in need thereof, i.e., the amount of drug needed to obtain the desired therapeutic effect. For example, a therapeutically effective amount for treating neuropathic pain is an amount of compound needed to, for example, reduce, suppress, eliminate or prevent the symptoms of neuropathic pain or to treat the underlying cause of neuropathic pain. On the other hand, the term "effective amount" means an amount sufficient to obtain a desired result, which may not necessary be a therapeutic result. For example, when studying a system comprising a norepinephrine transporter, an "effective amount" may be the amount needed to inhibit norepinephrine reuptake.

The term "treating" or "treatment" as used herein means the treating or treatment of a disease or medical condition (such as pulmonary arterial hypertension) in a patient, such as a mammal (particularly a human), that includes one or more of the following: (a) preventing the disease or medical condition from occurring, i.e., prophylactic treatment of a patient; (b) ameliorating the disease or medical condition, i.e., eliminating or causing regression of the disease or medical condition in a patient; (c) suppressing the disease or medical condition, i.e., slowing or arresting the development of the disease or medical condition in a patient; or (d) alleviating the symptoms of the disease or medical condition in a patient. For example, the term "treating pulmonary arterial hypertension" would include preventing pulmonary arterial hypertension from occurring, ameliorating pulmonary arterial hypertension, suppressing pulmonary arterial hypertension, and alleviating the symptoms of pulmonary arterial hypertension. The term "patient" is intended to include those mammals, such as humans, that are in need of treatment or disease prevention, that are presently being treated for disease prevention or treatment of a specific disease or medical condition, as well as test subjects in which compounds of the invention are being evaluated or being used in a assay, for example an animal model.

All other terms used herein are intended to have their ordinary meaning as understood by those of ordinary skill in the art to which they pertain.

GENERAL SYNTHETIC PROCEDURES

The crystalline compounds of the invention can be synthesized from readily available starting materials as described below and in the Examples. It will be appreciated that where typical or preferred process conditions (i.e., reaction temperatures, times, mole ratios of reactants, solvents, pressures, etc.) are given, other process conditions can also be used unless otherwise stated. It will be appreciated that while specific process conditions (i.e. crystallization temperatures, times, mole ratios of reactants, solvents, pressures, etc.) are given, other process conditions can also be used unless otherwise stated. In some instances, reactions or crystallizations were conducted at room temperature and no actual temperature measurement was taken. It is understood that room temperature can be taken to mean a temperature within the range commonly associated with the ambient temperature in a laboratory environment, and will typically be in the range of about 18° C. to about 30° C. In other instances, reactions or crystallizations were conducted at room temperature and the temperature was actually measured and recorded.

Generally, the crystallization is conducted in a suitable inert diluent or solvent system, examples of which include, but are not limited to, acetone, acetonitrile, ethyl acetate, methyl ethyl ketone, methanol, ethanol, isopropanol, isobutanol, dichloromethane, methyl t-butyl ether, cyclopentyl methyl ether, and the like, and mixtures thereof, optionally containing water. Mixtures of inert diluents include combinations such as acetone with water, acetonitrile with water, ethanol and ethyl acetate, methanol and water, and isopropanol and water. Upon completion of the crystallization, the crystalline compound can be isolated from the reaction mixture by any conventional means such as precipitation, concentration, centrifugation and the like.

The (S)-3-[(S)-2-methanesulfonyl-1-(4-trifluoromethylphenoxy)ethyl]pyrrolidine-1-carboxylic acid t-butyl ester starting material can be prepared by techniques that are well known in the art, and a specific example is provided in Example 1 (compound (c)). The (S)-3-[(S)-2-methanesulfonyl-1-(4-trifluoromethylphenoxy)ethyl]pyrrolidine starting material can be readily prepared by deprotecting this ester using hydrochloric acid. The molar ratios described in the methods of the invention can be readily determined by various methods available to those skilled in the art. For example, such molar ratios can be readily determined by $^1$H NMR. Alternatively, elemental analysis and HPLC methods can be used to determine the molar ratio.

Anhydrous Form I

In general, the anhydrous Form I can be prepared by treating a hydrochloride salt of (S)-3-[(S)-2-methanesulfonyl-1-(4-trifluoromethylphenoxy)ethyl]pyrrolidine with an inert diluent to complete dissolution. Alternately, the anhydrous Form I can be prepared by deprotecting (S)-3-[(S)-2-methanesulfonyl-1-(4-trifluoromethylphenoxy)ethyl]pyrrolidine-1-carboxylic acid t-butyl ester in the presence of an inert diluent to complete dissolution. Generally, dissolution is conducted at room temperature, which may range from about 18-30° C., and in one particular embodiment is conducted at a temperature of about 20° C. In one embodiment, the inert diluent is cyclopentyl methyl ether. In another embodiment, deprotection is done with hydrochloric acid (e.g., 3 M HCl) and the inert diluent is cyclopentyl methyl ether.

After a suitable amount of time, crystals will be observed. In one embodiment, crystals are observed over a period of about 1-3 days. After crystals are observed, the volume of the mother liquor can be reduced and the crystals isolated and dried. In one embodiment, the crystals are dried under nitrogen and under vacuum. In one embodiment, the crystals are isolated to yield a crystalline hydrochloride salt having purity typically about 99%.

Anhydrous Form II

In general, the anhydrous Form II can be prepared by treating a hydrochloride salt of (S)-3-[(S)-2-methanesulfonyl-1-(4-trifluoromethylphenoxy)ethyl]pyrrolidine with an inert diluent to complete dissolution. Generally, dissolution is conducted at room temperature, which may range from about 18-30° C., and in one particular embodiment is conducted at a temperature of about 20° C. In one embodiment, the inert diluent is cyclopentyl methyl ether.

The anhydrous Form II can also be prepared by treating the anhydrous Form I with an aqueous solution of an inert diluent to complete dissolution. Generally, dissolution is conducted at a room temperature, which may range from about 18-30° C., and in one particular embodiment is conducted at a temperature of about 20°. In one embodiment, the inert diluent is methyl t-butyl ether. The volume to volume ratio of methyl t-butyl ether to water can range from about 75:25 to about 95:5, and in one embodiment is within the range of 90:10 to about 95:5.

After a suitable amount of time, crystals will be observed. In one embodiment, crystals are observed over a period of about 2-4 days. After crystals are observed, the volume of the mother liquor can be reduced and the crystals isolated and dried. In one embodiment, the crystals are air dried under ambient conditions. In one embodiment, the crystals are isolated to yield a crystalline hydrochloride salt having purity typically about 99%.

Monohydrate

In general, the monohydrate can be prepared by treating the anhydrous Form I with water. In one embodiment, the monohydrate is prepared by exposing the anhydrous Form I to high humidity, ranging from about 65% to about 90% relative humidity, and in one particular embodiment, ranging from about 70% to about 80% relative humidity. Generally, the anhydrous Form I is exposed to the high humidity conditions from 12 to 48 hours, and in one embodiment, for about 24 hours.

CRYSTALLINE PROPERTIES

Among other advantages, it has been discovered that forming a crystalline hydrochloride salt of (S)-3-[(S)-2-methanesulfonyl-1-(4-trifluoromethylphenoxy)-ethyl]pyrrolidine, is useful for purifying the compound itself. For example, the crystalline hydrochloride salt anhydrous Form I has a purity of at least 99%.

As is well known in the field of powder x-ray diffraction, relative peak heights in PXRD patterns are dependent on a number of factors relating to sample preparation and instrument geometry, while peak positions are relatively insensitive to experimental details.

PXRD patterns and differential scanning calorimetry (DSC) thermograms were obtained, and thermogravimetric analysis (TGA) and dynamic moisture sorption (DMS) assessment (also known as a moisture sorption-desorption profile) were performed as described in Example 4. Thus, in one embodiment, the crystalline compounds are characterized by a PXRD pattern having certain peak positions. In another embodiment, the crystalline compounds are characterized by a DSC thermogram. In yet another embodiment, the crystalline compounds are characterized by a TGA trace.

Anhydrous Form I

The anhydrous Form I is characterized by a PXRD pattern in which the peak positions are substantially in accordance with those shown in FIG. 1. Sharp diffraction peaks were observed in the region 5-30 degrees in 2θ. Given that most peaks have low relative intensity, all peaks below 28° in 2θ are listed below.

| 2θ | d (Å) | Height[1] | H %[2] | * |
|---|---|---|---|---|
| 5.37 | 16.43 | 295 | 35.9 | * |
| 9.89 | 8.93 | 91 | 11.0 | * |
| 10.28 | 8.60 | 45 | 5.5 | * |
| 13.14 | 6.73 | 23 | 2.8 | |
| 13.53 | 6.54 | 35 | 4.3 | |
| 16.06 | 5.51 | 643 | 78.2 | * |
| 16.66 | 5.32 | 823 | 100.0 | * |
| 18.10 | 4.90 | 139 | 16.9 | |
| 18.36 | 4.83 | 83 | 10.1 | |
| 19.56 | 4.54 | 137 | 16.7 | |
| 19.90 | 4.46 | 522 | 63.5 | * |
| 21.46 | 4.14 | 383 | 46.5 | * |
| 21.88 | 4.06 | 113 | 13.8 | |
| 22.22 | 4.00 | 106 | 12.8 | |
| 23.18 | 3.83 | 301 | 36.6 | * |
| 24.12 | 3.69 | 42 | 5.1 | |
| 24.86 | 3.58 | 162 | 19.7 | |
| 25.36 | 3.51 | 87 | 10.5 | |
| 25.64 | 3.47 | 145 | 17.6 | |
| 26.58 | 3.35 | 130 | 15.8 | |
| 26.88 | 3.31 | 348 | 42.4 | * |
| 27.28 | 3.27 | 386 | 46.9 | * |
| 27.91 | 3.19 | 68 | 8.3 | |

[1]Peak height from base line
[2]Percent peak height compared to highest peak
* Indicates peaks that are important to identify this form Thus, in one embodiment, the anhydrous Form I is characterized by a PXRD pattern comprising diffraction peaks at 2θ values of 5.37±0.20, 9.89±0.20, 10.28±0.20, 16.06±0.20, 16.66±0.20, 19.90±0.20, 21.46±0.20, 23.18±0.20, 26.88±0.20, and 27.28±0.20; and further characterized by having one or more additional diffraction peaks at 2θ values selected from 13.14±0.20, 13.53±0.20, 18.10±0.20, 18.36±0.20, 19.56±0.20, 21.88±0.20, 22.22±0.20, 24.12±0.20, 24.86±0.20, 25.36±0.20, 25.64±0.20, 26.58±0.20, and 27.91±0.20.

Figure 2:
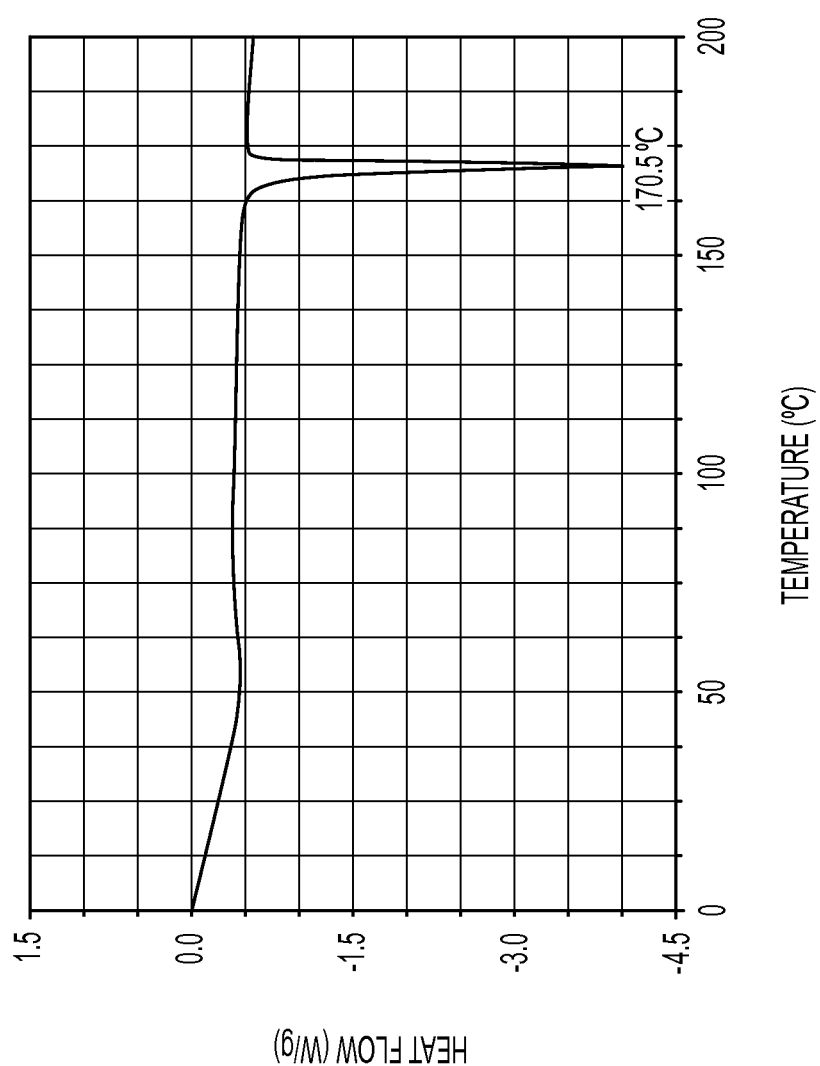
FIG. 2 shows a differential scanning calorimetry (DSC) thermogram.

In one embodiment, the anhydrous Form I is characterized by the DSC thermogram in FIG. 2. The DSC thermogram demonstrates that the anhydrous Form I exhibits a sharp melting endotherm in the range of about 169-172° C.; for example FIG. 2 shows an endotherm of about 170.5° C. A shallow endotherm is observed near 52° C., which may correspond to moisture or solvent adhered to the particles. No other thermal events were observed prior to the melting transition.

Figure 3:
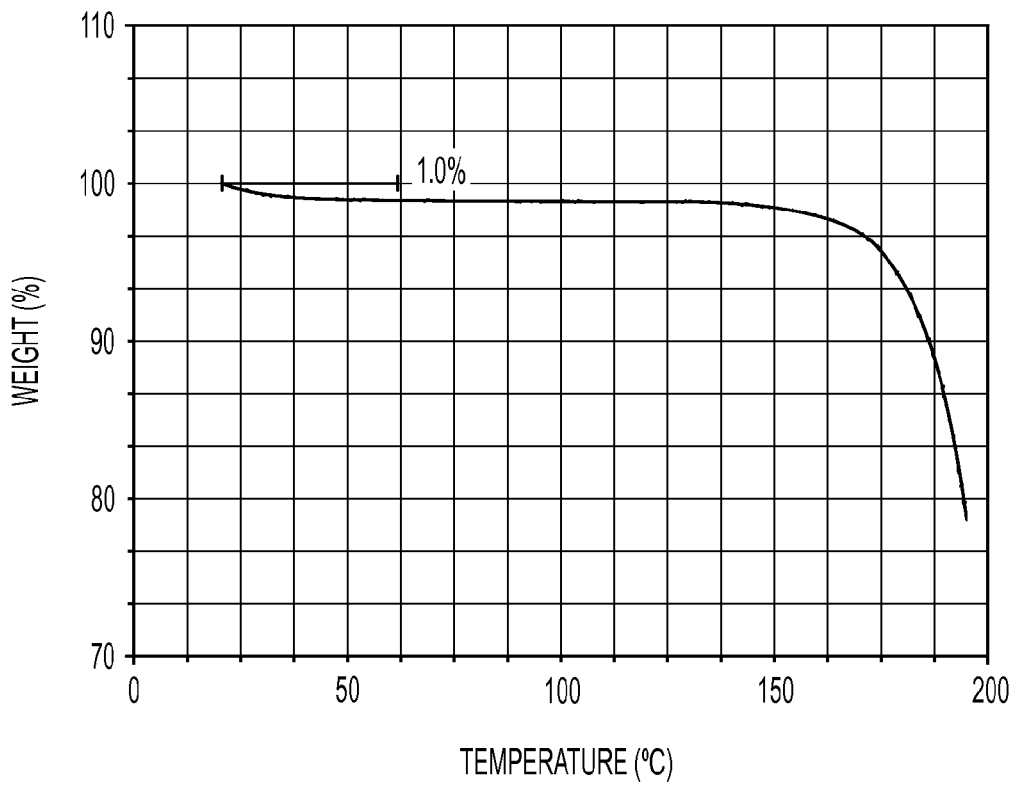
FIG. 3 shows a thermal gravimetric analysis (TGA) trace.

In one embodiment, the anhydrous Form I is characterized by the TGA trace in FIG. 3. The TGA trace shows an early loss of mass of approximately 1.0 weight percent (corresponding to the shallow endotherm seen the DSC thermogram). Otherwise no other weight loss is observed until after melting. The anhydrous Form I decomposes after melting, as evidenced by significant weight loss after about 160° C.

Figure 4:
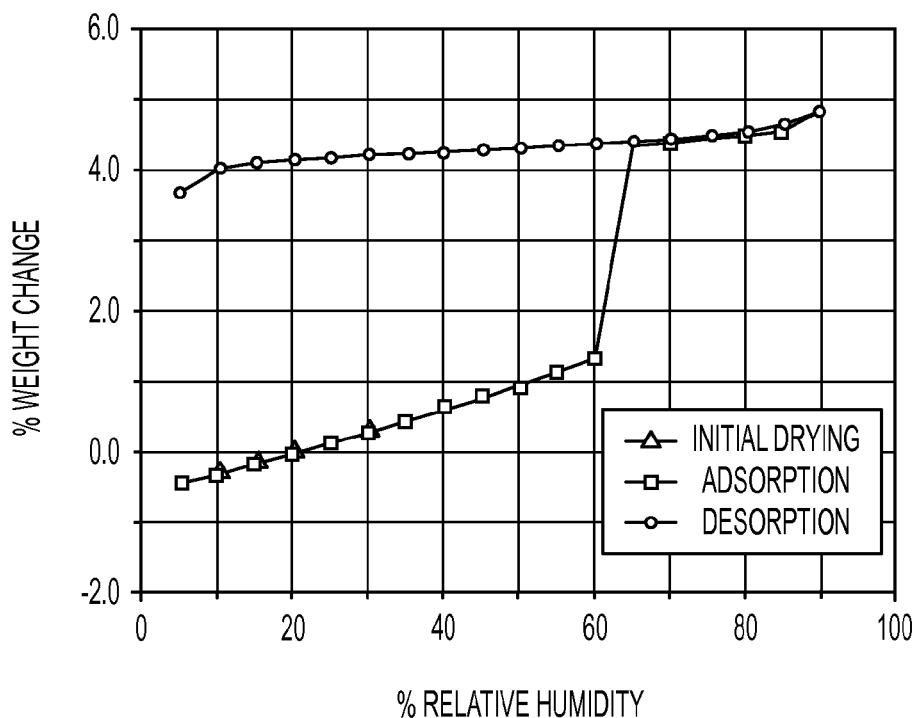
FIG. 4 shows a dynamic moisture sorption (DMS) profile.
Figure 5:
FIG. 5 is a polarized light microscopic (PLM) image.

In one embodiment, the anhydrous Form I is characterized by the DMS profile in FIG. 4. This DMS profile demonstrates that during the adsorption segment, the anhydrous Form I takes up moisture gradually until 60% RH. Between 60% RH and 65% RH the moisture uptake is rapid. The isotherm remains flat in the region of 65% RH to 90% RH. During the desorption segment, the anhydrous Form I does not lose the moisture gained during the adsorption, i.e., after completion of the DMS experiment, the anhydrous Form I is converted to the monohydrate form (as characterized by PXRD, DSC, and TGA). In another embodiment, the anhydrous Form I is characterized by the polarized light microscopic (PLM) image in FIG. 5, which shows the anhydrous Form I as being birefringent with plate-like crystals.

Anhydrous Form II

Figure 6:
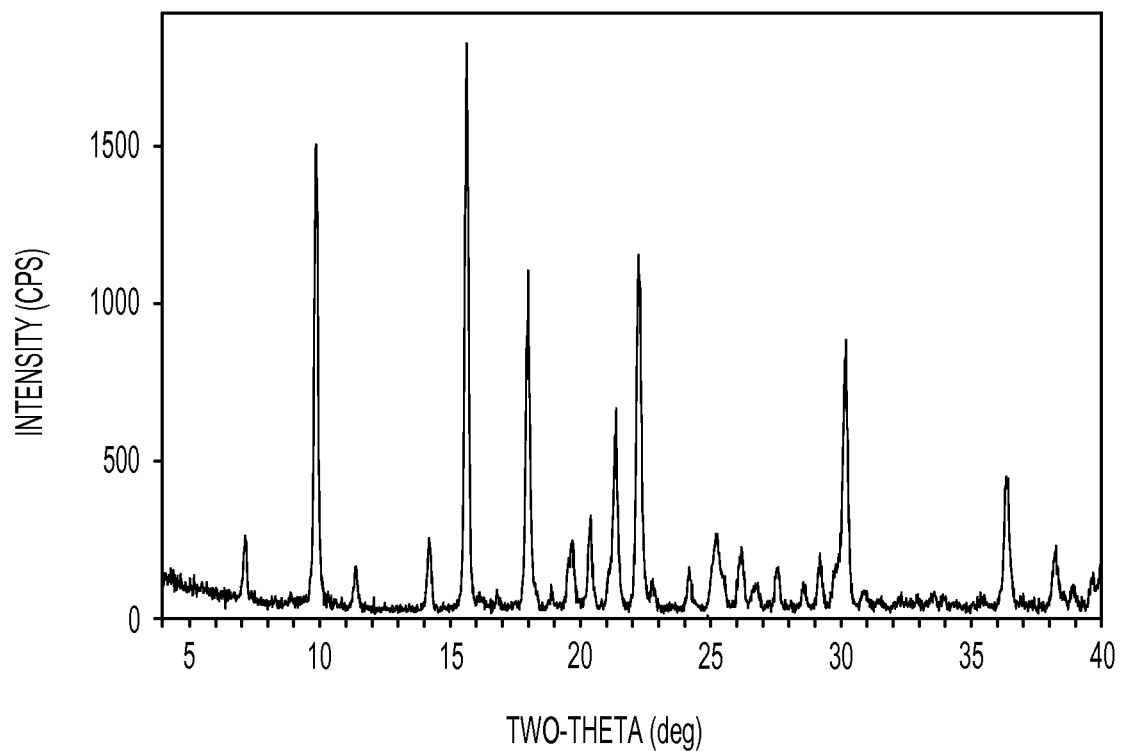
FIGS. 6-7 show PXRD patterns of the crystalline hydrochloride anhydrous Form II salt of (S)-3-[(S)-2-methanesulfonyl-1-(4-trifluoromethylphenoxy)ethyl]pyrrolidine.

The anhydrous Form II is characterized by a PXRD pattern in which the peak positions are substantially in accordance with those shown in FIG. 6. Sharp diffraction peaks were observed in the region 5-40 degrees in 2θ. Peak positions appear at different 2θ values (compared to those of the anhydrous Form I) indicating that this pattern belongs to a different polymorph. Peaks with intensities greater than 10% by height are listed below (except the peak at 11.4° in 2θ).

| 2θ | d (Å) | Height[1] | H %[2] | * |
|---|---|---|---|---|
| 7.14 | 12.37 | 204 | 11.4 | * |
| 9.86 | 8.96 | 1461 | 81.6 | * |
| 11.38 | 7.77 | 130 | 7.3 | * |
| 14.20 | 6.23 | 227 | 12.7 | * |
| 15.64 | 5.66 | 1791 | 100.0 | * |
| 18.00 | 4.92 | 1072 | 59.8 | * |
| 19.70 | 4.50 | 208 | 11.6 | |
| 20.40 | 4.35 | 279 | 15.6 | |
| 21.38 | 4.15 | 624 | 34.8 | * |
| 22.24 | 3.99 | 1115 | 62.2 | * |
| 25.20 | 3.53 | 233 | 13.0 | |
| 26.18 | 3.40 | 188 | 10.5 | |
| 30.20 | 2.96 | 836 | 46.7 | * |
| 36.36 | 2.47 | 413 | 23.1 | * |
| 38.26 | 2.35 | 194 | 10.8 | |

[1]Peak height from base line
[2]Percent peak height compared to highest peak
* Indicates peaks that are important to identify this form Thus, in one embodiment, the anhydrous Form II is characterized by a PXRD pattern comprising diffraction peaks at 2θ values of 7.14±0.20, 9.86±0.20, 11.38±0.20, 14.20±0.20, 15.64±0.20, 18.00±0.20, 21.38±0.20, 22.24±0.20, 30.20±0.20, and 36.36±0.20; and further characterized by having one or more additional diffraction peaks at 2θ values selected from 19.70±0.20, 20.40±0.20, 25.20±0.20, 26.18±0.20, and 38.26±0.20.

Figure 7:
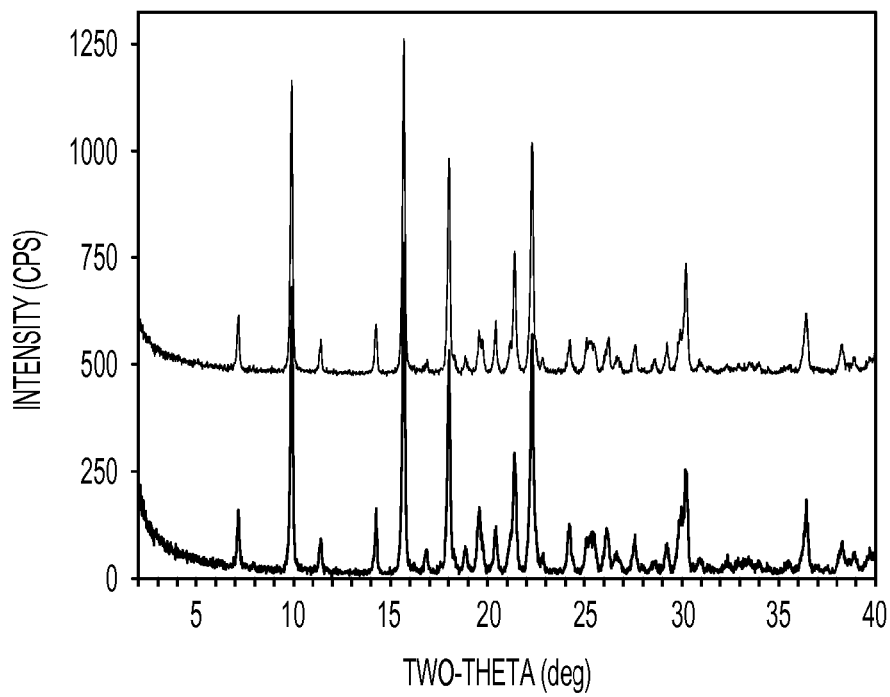

A sample of the anhydrous Form II was recrystallized in isopropyl alcohol. FIG. 7 depicts the overlay of the PXRD patterns of the starting anhydrous Form II material and the recrystallized product, showing the same peaks as evidence that the materials are the same form.

Figure 8:
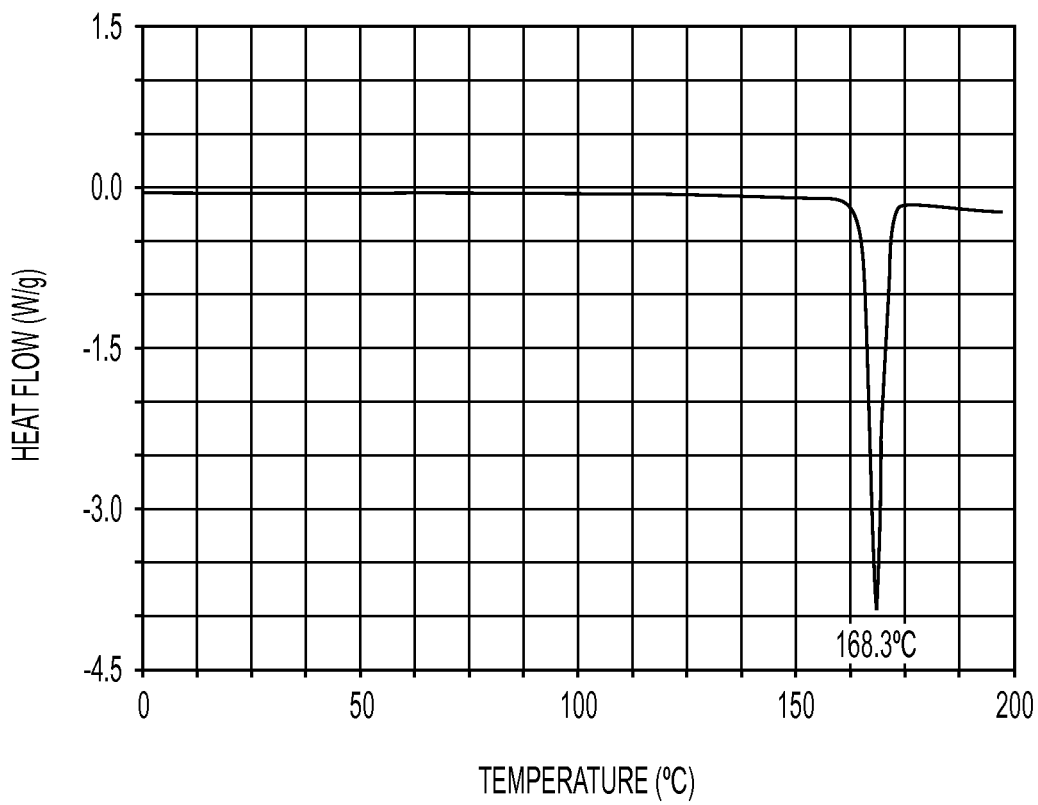
FIG. 8 shows a DSC thermogram.
Figure 9:
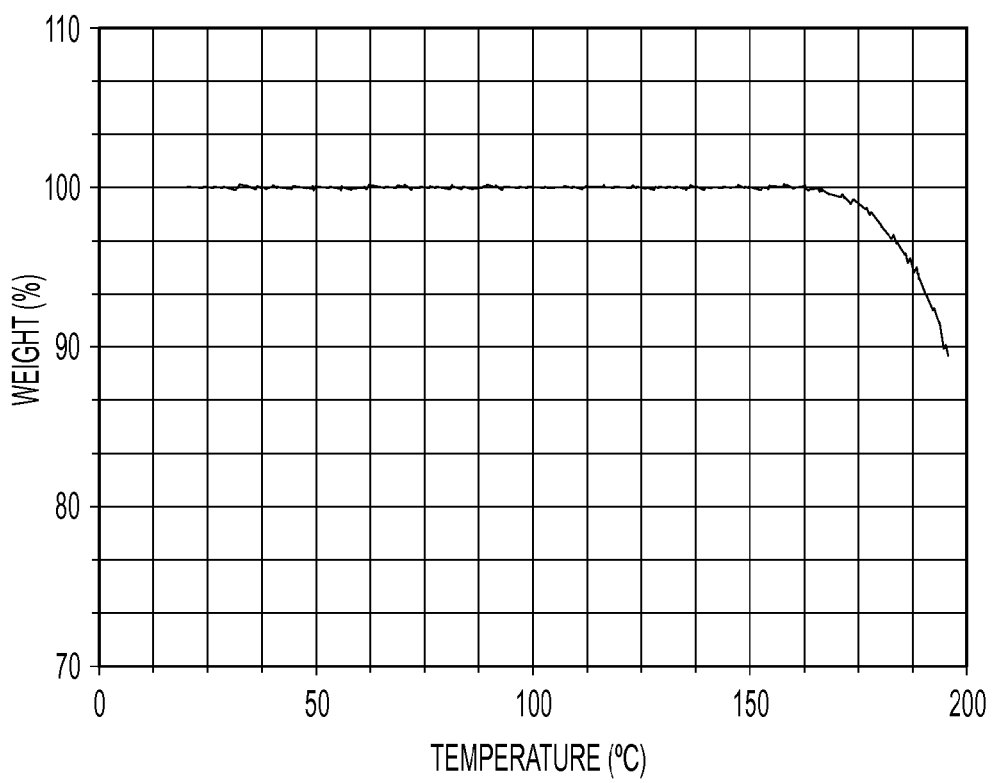
FIG. 9 shows a TGA trace.

In one embodiment, the anhydrous Form II is characterized by the DSC thermogram in FIG. 8. The DSC thermogram demonstrates that the anhydrous Form II has a sharp melting endotherm in the range of about 166.2-169.2° C.; for example FIG. 9 shows an endotherm of about 168.3° C. No other thermal events were observed prior to the melting transition. In comparing this thermogram to that of the anhydrous Form I (FIG. 2), it is noted that the anhydrous Form II does not appear to retain surface adsorbed moisture and that the anhydrous Form II has a slightly lower melting point than that of anhydrous Form I.

In one embodiment, the anhydrous Form II is characterized by the TGA trace in FIG. 9. The TGA trace did not show any weight loss prior to the post-melting decomposition, which was consistent with the DSC thermogram.

Figure 10:
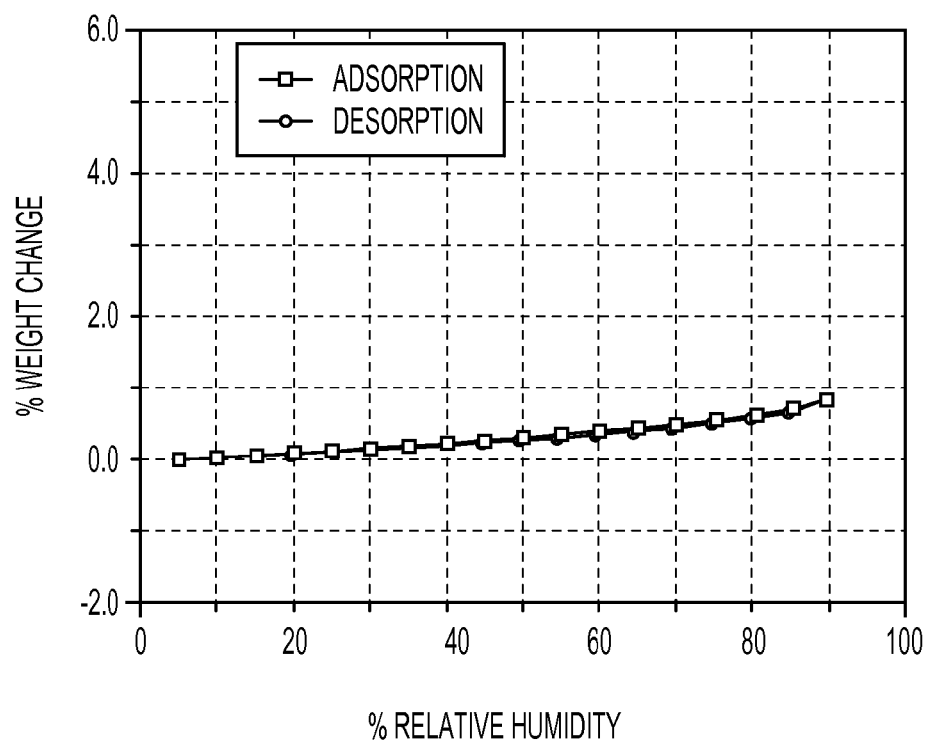
FIG. 10 shows a DMS profile.

In one embodiment, the anhydrous Form II is characterized by the DMS profile in FIG. 10. This DMS profile demonstrates that during the adsorption segment from 5% RH to 90% RH, the anhydrous Form II picks up less than 1% by weight of moisture and the desorption profile matches with the adsorption profile. There is no hysteresis in the two segments indicating that the small amount of moisture taken up by the anhydrous Form II corresponds to the surface adsorption. There is no change in the form after the DMS experiment; the anhydrous Form II remains as Form II (as characterized by PXRD, DSC, and TGA).

Figure 11:
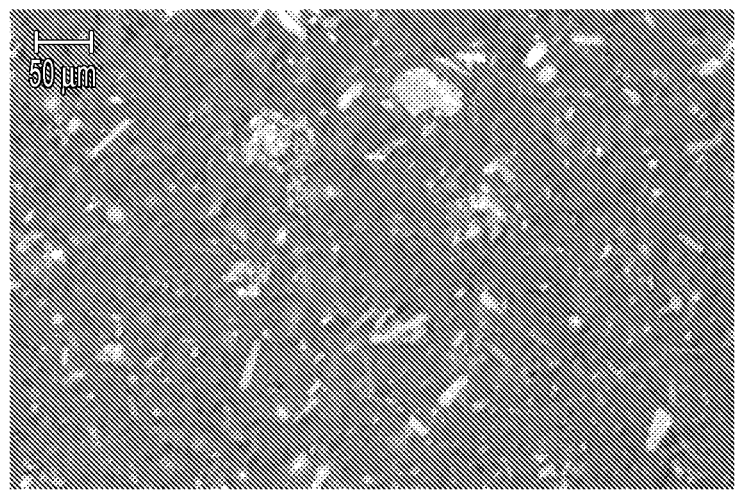
FIG. 11 is a PLM image.

In another embodiment, the anhydrous Form II is characterized by the PLM image in FIG. 11, which shows the anhydrous Form II as being birefringent with lath-like crystals.

Monohydrate

Figure 12:
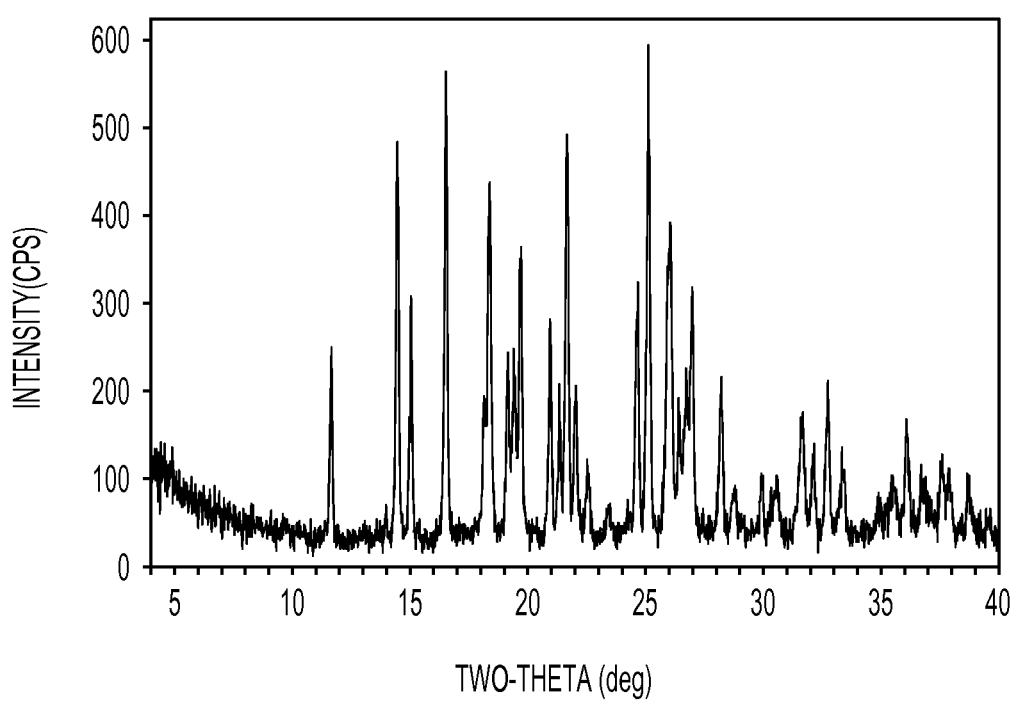
FIG. 12 shows a PXRD pattern of the crystalline hydrochloride monohydrate salt of (S)-3-[(S)-2-methanesulfonyl-1-(4-trifluoromethylphenoxy)ethyl]pyrrolidine.

The monohydrate is characterized by a PXRD pattern in which the peak positions are substantially in accordance with those shown in FIG. 12. Sharp diffraction peaks were observed in the region 10-40 degrees in 2θ. Peak positions appear at different 2θ values (compared to those of the anhydrous Form I and the anhydrous Form II) indicating that this pattern belongs to a different crystalline form. Peaks with intensities greater than 20% by height are listed below.

| 2θ | d (Å) | Height[1] | H %[2] | * |
|---|---|---|---|---|
| 11.54 | 7.66 | 110 | 31.2 | * |
| 14.38 | 6.15 | 304 | 86.3 | * |
| 14.96 | 5.92 | 173 | 49.1 | * |
| 16.44 | 5.39 | 321 | 91.3 | * |
| 18.30 | 4.84 | 299 | 84.8 | * |
| 19.08 | 4.65 | 152 | 43.2 | |
| 19.36 | 4.58 | 138 | 39.2 | |
| 19.62 | 4.52 | 239 | 67.8 | * |
| 20.88 | 4.25 | 175 | 49.7 | |
| 21.23 | 4.18 | 89 | 25.2 | |
| 21.56 | 4.12 | 352 | 100.0 | * |
| 21.92 | 4.05 | 83 | 23.7 | |
| 24.56 | 3.62 | 239 | 67.8 | * |
| 25.06 | 3.55 | 328 | 93.0 | * |
| 25.96 | 3.43 | 329 | 93.4 | * |
| 26.36 | 3.38 | 109 | 30.9 | |
| 26.66 | 3.34 | 157 | 44.7 | |
| 26.92 | 3.31 | 210 | 59.6 | * |
| 28.06 | 3.18 | 127 | 36.0 | |
| 28.67 | 3.11 | 73 | 20.6 | |
| 30.44 | 2.93 | 72 | 20.4 | |
| 31.62 | 2.83 | 120 | 34.0 | |
| 32.02 | 2.79 | 75 | 21.2 | |
| 32.60 | 2.74 | 112 | 31.7 | |
| 33.25 | 2.69 | 100 | 28.3 | |
| 36.02 | 2.49 | 73 | 20.7 | |

[1]Peak height from base line
[2]Percent peak height compared to highest peak
* Indicates peaks that are important to identify this form Thus, in one embodiment, the monohydrate is characterized by a PXRD pattern comprising diffraction peaks at 2θ values of 11.54±0.20, 14.38±0.20, 14.96±0.20, 16.44±0.20, 18.30±0.20, 19.62±0.20, 21.56±0.20, 24.56±0.20, 25.06±0.20, 25.96±0.20, and 26.92±0.20; and further characterized by having one or more additional diffraction peaks at 2θ values selected from 19.08±0.20, 19.36±0.20, 20.88±0.20, 21.23±0.20, 21.92±0.20, 26.36±0.20, 26.66±0.20, 28.06±0.20, 28.67±0.20, 30.44±0.20, 31.62±0.20, 32.02±0.20, 32.60±0.20, 33.25±0.20, and 36.02±0.20.

Figure 13:
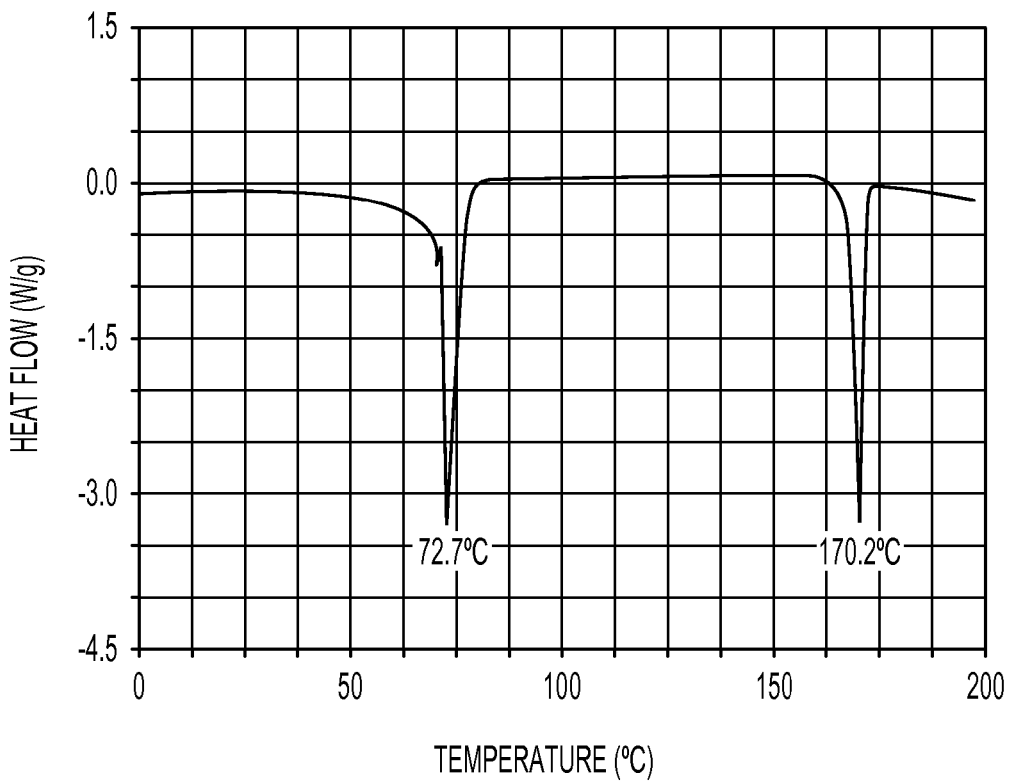
FIG. 13 shows a DSC thermogram.

In one embodiment, the monohydrate is characterized by the DSC thermogram in FIG. 13. The DSC thermogram demonstrates that the monohydrate has two sharp endotherms. A dehydration endotherm peak is observed in the range of about 71.2 to 74.2° C. and a melting endotherm peak is observed in the range of about 168.7-171.7° C.; for example FIG. 2 shows a dehydration endotherm peak at about 73° C. and an endotherm peak of about 170.2°.

Figure 14:
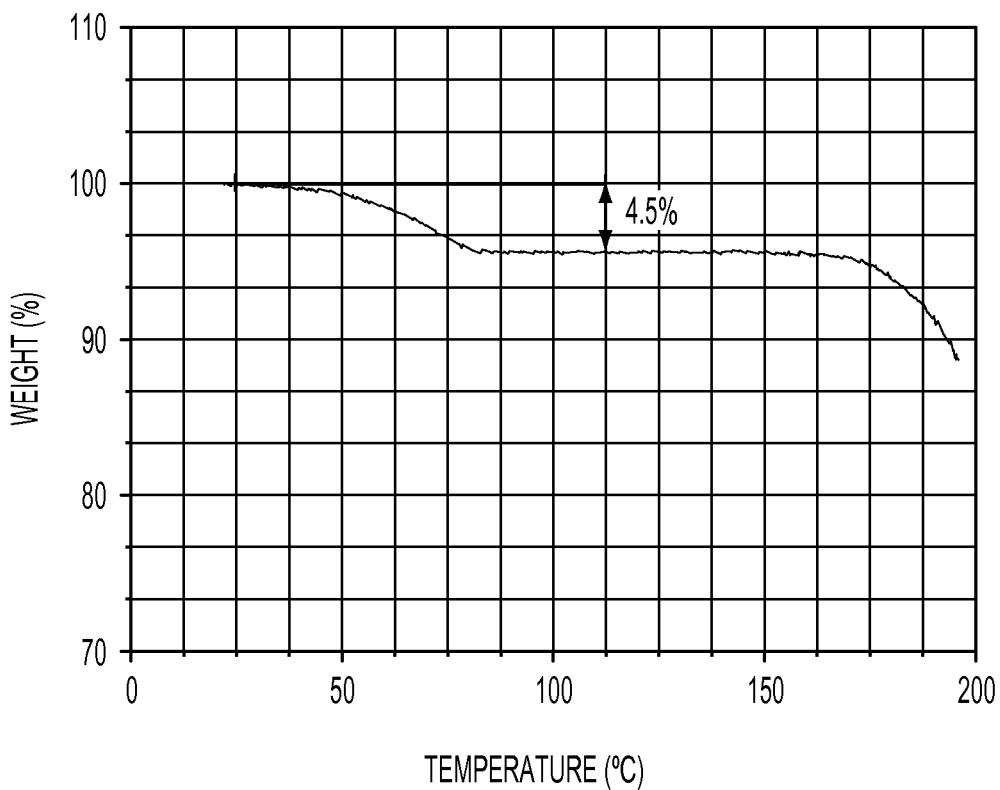
FIG. 14 shows a TGA trace.

In one embodiment, the monohydrate is characterized by the TGA trace in FIG. 14.

The TGA trace shows a loss of mass of about 4.5 weight percent in the region of 30-80° C. The mass lost corresponds to 1 equivalent of water, noting that the expected weight loss for a monohydrate is generally about 4.6%.

Figure 15:
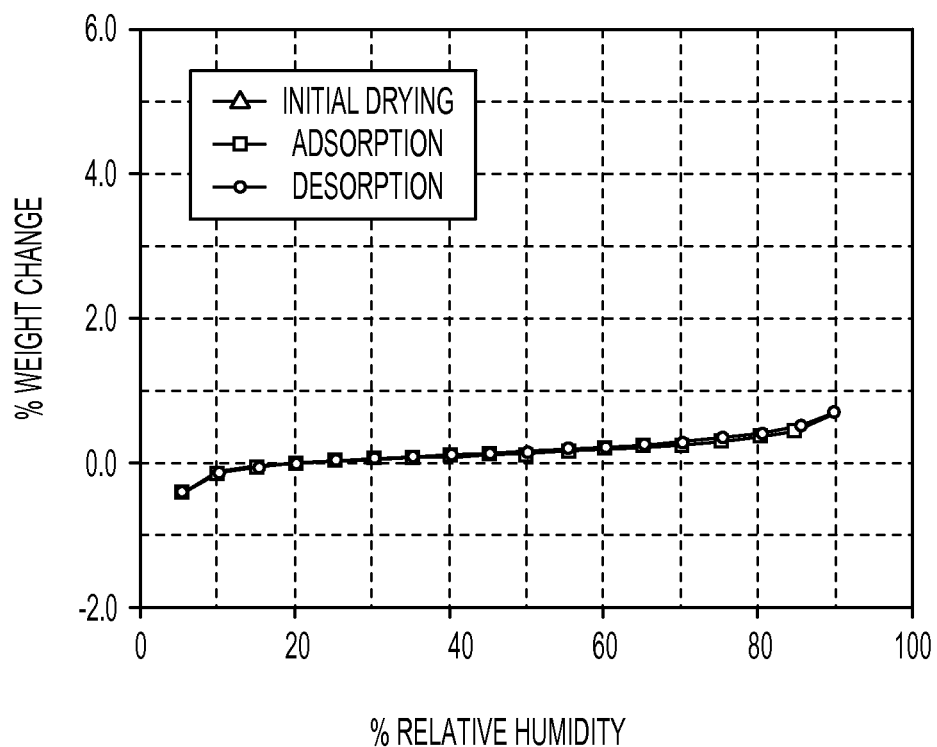
FIG. 15 shows a DMS profile.

In one embodiment, the monohydrate is characterized by the DMS profile in FIG. 15. This DMS profile demonstrates that during the adsorption segment from 5% RH to 90% RH, the monohydrate picks up less than 1% by weight of moisture and the desorption profile matches with the adsorption profile. There is no hysteresis in the two segments indicating that the small amount of moisture taken up by the monohydrate corresponds to the surface adsorption. There is no change in the form after the DMS experiment, i.e., the monohydrate remains as the monohydrate form (as characterized by PXRD, DSC, and TGA).

Figure 16:
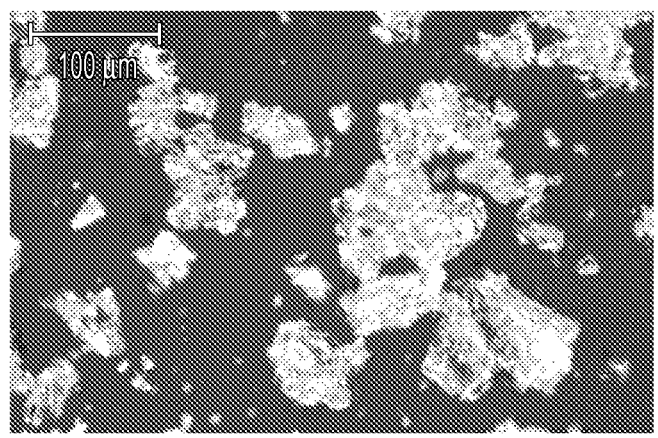
FIG. 16 is a PLM image.

In another embodiment, the monohydrate is characterized by the PLM image in FIG. 16, which shows the monohydrate as being birefringent, indicating crystallinity.

These properties of the crystalline compounds of the invention are further illustrated in the Examples below.

UTILITY (S)-3-[(S)-2-methanesulfonyl-1-(4-trifluoromethylphenoxy)ethyl]pyrrolidine possesses serotonin reuptake inhibition activity. Thus, this compound, as well as of the crystalline compounds of the invention, is expected to have therapeutic utility as a serotonin reuptake inhibitor.

Exemplary assays to determine the serotonin reuptake inhibiting activity of the crystalline compounds of the invention include by way of illustration and not limitation, assays that measure SERT binding, for example, as described in Tsuruda et al. (2010) *Journal of Pharmacological and Toxicological Methods* 61(2):192-204. Useful secondary assays include neurotransmitter uptake assays to measure inhibition of serotonin uptake into cells expressing the human or rat recombinant transporter and ex vivo radioligand binding assays that are used to determine the in vivo occupancy of SERT in tissue. Other assays that are useful to evaluate pharmacological properties of test compounds include, but are not limited to, cold ligand binding kinetics assays (Motulsky and Mahan (1984) *Molecular Pharmacol.* 25(1):1-9) with membranes prepared from cells expressing hSERT conventional membrane radioligand binding assays using radiolabeled, for example, tritiated, test compound; radioligand binding assays using native tissue from, for example rodent or human brain; neurotransmitter uptake assays using human or rodent platelets; and neurotransmitter uptake assays using crude, or pure, synaptosome preparations from rodent brain.

Exemplary in vivo assays include the rat peripheral serotonin model described, for example, in Ortiz et al. (1992) *British Journal of Pharmacology* 105:941-946; and the rat serotonin syndrome model described, for example, in Izumi et al. (2006) *European Journal of Pharmacology* 532:258-264. The rat monocrotaline model of pulmonary arterial hypertension is described, for example, in Kato et al. (2008) *J. Cardiovasc. Pharmacol.* 51(1):18-23, which is a reliable predictor of clinical efficacy for the treatment of pulmonary arterial hypertension. Platelet aggregation assays are described for example, in Carneiro et al. (2008) *J. Clin. Invest.* 118(4):1544-1552. Thrombosis can be measured by several models, including the arterial thrombosis rodent model described, in Krekora et al. (1999) *Thrombosis Research* 96:407-414, and the rodent model of microarterial anastomosis, described in Nayak et al (2005) *Arch Otolaryngol Head Meck Surg.* 131:800-803). The mouse hypoxia model is also useful to evaluate the compounds of the invention, and is described for example, in Marcos et al., (2003) *Am. J Respir. Crit. Care Med.*

168:487-493. The aforementioned assays are useful in determining the therapeutic utility. Other properties and utilities of compounds of the invention can be demonstrated using various in vitro and in vivo assays well known to those skilled in the art.

The crystalline compounds of the invention are expected to be useful for the treatment and/or prevention of medical conditions in which the regulation of peripheral monoamine transporter function is implicated, in particular those conditions mediated by or responsive to the inhibition of serotonin reuptake. Thus it is expected that patients suffering from a disease or disorder that is treated by the inhibition of the serotonin transporter can be treated by administering a therapeutically effective amount of a crystalline compound of the invention.

The amount of active agent administered per dose or the total amount administered per day may be predetermined or it may be determined on an individual patient basis by taking into consideration numerous factors, including the nature and severity of the patient's condition, the condition being treated, the age, weight, and general health of the patient, the tolerance of the patient to the active agent, the route of administration, pharmacological considerations such as the activity, efficacy, pharmacokinetics and toxicology profiles of the active agent and any secondary agents being administered, and the like. Treatment of a patient suffering from a disease or medical condition (such as pulmonary arterial hypertension) can begin with a predetermined dosage or a dosage determined by the treating physician, and will continue for a period of time necessary to prevent, ameliorate, suppress, or alleviate the symptoms of the disease or medical condition. Patients undergoing such treatment will typically be monitored on a routine basis to determine the effectiveness of therapy. For example, in treating pulmonary arterial hypertension, a measure of the effectiveness of treatment may involve assessment of the patient's quality of life, e.g., improvements in the patient's sleeping patterns, work attendance, ability to exercise and be ambulatory, etc. Indicators for the other diseases and conditions described herein, are well-known to those skilled in the art, and are readily available to the treating physician. Continuous monitoring by the physician will insure that the optimal amount of active agent will be administered at any given time, as well as facilitating the determination of the duration of treatment. This is of particular value when secondary agents are also being administered, as their selection, dosage, and duration of therapy may also require adjustment. In this way, the treatment regimen and dosing schedule can be adjusted over the course of therapy so that the lowest amount of active agent that exhibits the desired effectiveness is administered and, further, that administration is continued only so long as is necessary to successfully treat the disease or medical condition.

Pulmonary Arterial Hypertension (PAH)

Compounds having serotonin reuptake inhibiting activity have been shown to prevent or reverse PAH in animal models. See, for example, Zhu et al. (2009) *Clinical and Experimental Pharmacology and Physiology* 36(8): e1-e5 and Shah et al. (2009) *Chest* 136(3):694-700. Thus, the crystalline compounds are expected to find utility in treating PAH, as well as potentially finding utility in preventing disease progression. In addition, these crystalline compounds are expected to find utility in treating PAH associated with chronic obstructive pulmonary disease (COPD); see, for example, Chaouat et al. (2009) Chest 136:3. For treatment of PAH, the therapeutically effective amount is typically the amount that is sufficient to lower the pulmonary vascular resistance. Other goals of therapy are to improve a patient's exercise capacity and to decrease mortality associated with PAH. For example, in a clinical setting, the therapeutically effective amount can be the amount that improves a patient's ability to walk comfortably for a period of 6 minutes (covering a distance of approximately 20-40 meters). When used for treating this disorder, the crystalline compounds may be administered with secondary agents, including by way of illustration and not limitation, a-adrenergic antagonists, $\beta_1$-adrenergic receptor antagonists, $\beta_2$-adrenergic receptor agonists, angiotensin-converting enzyme inhibitors, anticoagulants, calcium channel blockers, diuretics, endothelin receptor antagonists, PDE-5 inhibitors, prostaglandin analogs, and combinations thereof

Thrombosis-induced Cardiovascular Diseases

Serotonin has been found to play a role in platelet activation (See, for example, Walther et al. (2003) *Cell* 115:851-862). Thus, the crystalline compounds are expected to find utility in anti-platelet therapy, in particular for treatment of: thrombosis-induced cardiovascular diseases such as: atherosclerosis; cerebrovascular diseases such as stroke; congestive heart failure; coronary artery disease such as angina; myocardial infarction (heart attack) and other forms of ischemic heart disease; metabolic syndrome (Syndrome X); peripheral vascular disease; pulmonary embolism; thrombosis, including peripheral vascular thrombosis; and thrombotic re-occlusion that may occur after surgery. When used for treating such disorders, the crystalline compounds may be administered in combination with one or more other anti-thrombotic agents.

Gastrointestinal Disorders

It has been found that abnormalities in serotonin reuptake can alter enteric serotonergic signaling, leading to sensory, motor, and secretory gut dysfunctions. See, for example, Colucci et al. (2008) *Trends in Molecular Medicine* 14(7): 295-304. Thus, the crystalline compounds are expected to find utility in treating gastrointestinal disorders in the mid or lower gastrointestinal tract. These include, for example, irritable bowel syndrome, diarrhea-predominant irritable bowel syndrome, dyspepsia, functional abdominal bloating, functional constipation, and functional diarrhea. When used for treating gastrointestinal disorders, the crystalline compounds may be administered with secondary agents, including by way of illustration and not limitation, anti-diarrheals, antispasmodic agents (e.g., anticholinergics and smooth muscle relaxants), and combinations thereof.

Cancer

Recent studies have indicated that the serotonin neurotransmitter transporter plays a role in cancer. See, for example, Gil-Ad et al (2008) *International Journal of Oncology* 33:277-286 and Amit et al. *European Neuropsychopharmacology* (2009) 19:726-734. Thus, the crystalline compounds are expected to find utility as anti-proliferative agents in treating cancer such as colorectal cancer and leukemia, and may be administered with secondary agents such as antineoplastic agents, anti-proliferative agents, cytotoxic agents, tumor growth inhibitors, and combinations thereof.

Rheumatoid Arthritis

Compounds having serotonin reuptake inhibiting activity have been shown to exhibit anti-inflammatory properties (Roumestan et al. (2007) *Respiratory Research* 8:35), more particularly in a rheumatoid arthritis animal model (Sacre et al. (2010) *Arthritis & Rheumatism* 62(3):683-693). Thus, the crystalline compounds are expected to find utility in the treatment of rheumatoid arthritis, and may be administered with secondary agents such as corticosteroids; disease modifying anti-rheumatic drugs including hydroxychloroquine, leflunomide, methotrexate, sulfasalazine, gold salts such as intramuscular gold, interleukin-1 receptor antagonist therapies such as anakinra, B cell depleting agents such as rituximab, T-cell costimulatory blocking agents such as abatacept, tumor necrosis factor inhibitors such as adalimumab, etanercept, and infliximab, and immunomodulatory and cytotoxic agents such as azathioprine, cyclophosphamide, and cyclosporine A; non-steroidal anti-inflammatory agents; and combinations thereof.

Osteoarthritis

The serotonin reuptake inhibitor, duloxetine, has been shown to be useful in reducing pain severity in patients with osteoarthritis pain of the knee. Thus, the crystalline compounds are expected to find utility in the treatment of osteoarthritis, and may be administered with secondary agents such as analgesics (e.g., acetaminophen), corticosteroids, non-steroidal anti-inflammatory agents; and combinations thereof.

Osteoporosis

Gut-derived serotonin has been proposed to inhibit bone formation. Recent studies have explored whether affecting the biosynthesis of gut-derived serotonin could treat osteoporosis by increasing bone formation, and concluded that inhibiting such biosynthesis could become a new treatment for osteoporosis (Yadav et al. *Nature Medicine* (2010) 16:308-312). Thus, the crystalline compounds are also expected to find utility in the treatment of osteoporosis.

Diabetes

The selective serotonin reuptake inhibitor, s-citalopram, has been shown to be useful in treating patients with co-morbid major depression and diabetes mellitus, showing a potential ability to improve glycemic control (Amsterdam et al. (2006) *Neuropsychobiology* 54:208-214). Studies with the selective serotonin reuptake inhibitor, fluvoxamine, suggest that such compounds may find utility in reducing postprandial hyperglycemia (Moore et al. (2005) *Am. J. Physiol. Endocrinol. Metab.* 288:E556-E563). Thus, the crystalline compounds are also expected to find utility in the treatment of diabetes, and may be administered with orally effective antibiotic secondary agents such as: biguanides such as metformin; glucagon antagonists; α-glucosidase inhibitors such as acarbose and miglitol; dipeptidyl peptidase IV inhibitors (DPP-IV inhibitors) such as alogliptin, denagliptin, linagliptin, saxagliptin, sitagliptin, and vildagliptin; meglitinides such as repaglinide; oxadiazolidinediones; sulfonylureas such as chlorpropamide, glimepiride, glipizide, glyburide, and tolazamide; thiazolidinediones such as pioglitazone and rosiglitazone; and combinations thereof.

Research Tools

The crystalline compounds of the invention are also expected to be useful as a research tool for investigating or studying biological systems or samples having serotonin transporters. Any suitable biological system or sample having serotonin transporters may be employed in such studies, which may be conducted either in vitro or in vivo. Representative biological systems or samples suitable for such studies include, but are not limited to, cells, cellular extracts, plasma membranes, tissue samples, isolated organs, mammals (such as mice, rats, guinea pigs, rabbits, dogs, pigs, humans, and so forth), and the like, with mammals being of particular interest. In one particular embodiment of the invention, serotonin reuptake in a mammal is inhibited by administering a serotonin reuptake-inhibiting amount of a crystalline compound. The crystalline compounds can also be used as research tools by conducting biological assays using such compound.

When used as a research tool, a biological system or sample comprising a serotonin transporter is typically contacted with a serotonin reuptake-inhibiting amount of a crystalline compound. After the biological system or sample is exposed to the crystalline compound, the effects of inhibiting serotonin reuptake are determined using conventional procedures and equipment. Exposure encompasses contacting cells or tissue with the compound, administering the compound to a mammal, for example by i.p. or i.v. administration, by the use of an implantable pump such as the Alzet® osmotic pump, and so forth. This determining step may comprise measuring a response, i.e., a quantitative analysis or may comprise an observation, i.e., a qualitative analysis. Measuring a response involves, for example, determining the effects of the compound on the biological system or sample using conventional procedures and equipment, such as a serotonin reuptake assay. The assay results can be used to determine the activity level as well as the amount of compound necessary to achieve the desired result, i.e., a serotonin reuptake-inhibiting amount.

Additionally, the crystalline compounds can be used as a research tools for evaluating other chemical compounds, and is thus useful in screening assays to discover, for example, new compounds having serotonin reuptake-inhibiting activity. In this manner, a crystalline compound is used as a standard in an assay to allow comparison of the results obtained with a test compound and with the crystalline compound to identify those test compounds that have about equal or superior reuptake-inhibiting activity, if any.

For example, reuptake data for a test compound or a group of test compounds is compared to the reuptake data for the crystalline compound to identify those test compounds that have the desired properties, e.g., test compounds having reuptake-inhibiting activity about equal or superior to the crystalline compound, if any. This aspect of the invention includes, as separate embodiments, both the generation of comparison data (using the appropriate assays) and the analysis of the test data to identify test compounds of interest. Thus, a test compound can be evaluated in a biological assay, by a method comprising the steps of: (a) conducting a biological assay with a test compound to provide a first assay value; (b) conducting the biological assay with the crystalline compound of the invention to provide a second assay value; wherein step (a) is conducted either before, after or concurrently with step (b); and (c) comparing the first assay value from step (a) with the second assay value from step (b). Exemplary biological assays include serotonin reuptake assays.

PHARMACEUTICAL COMPOSITIONS AND FORMULATIONS

The crystalline compounds of the invention are typically administered to a patient in the form of a pharmaceutical composition or formulation. Such pharmaceutical compositions may be administered to the patient by any acceptable route of administration including, but not limited to, oral, rectal, vaginal, nasal, inhaled, topical (including transdermal) and parenteral modes of administration. However, it will be understood by those skilled in the art that, once a crystalline compound has been formulated, it may no longer be in crystalline form, i.e., it may be dissolved in a suitable carrier. Further, the crystalline compound may be administered, for example orally, in multiple doses per day (e.g., twice, three times or four times daily), in a single daily dose, in a twice daily dose, in a single weekly dose, and so forth.

In general, pharmaceutical compositions are prepared by combining one or more pharmaceutically acceptable carriers with a crystalline compound of the invention. Accordingly, in one embodiment, the invention relates to a pharmaceutical composition comprising a pharmaceutically acceptable carrier and a crystalline compound of the invention. The compositions may contain other therapeutic and/or formulating agents if desired. When discussing compositions, a "crystalline compound of the invention" may also be referred to herein as an "active agent," to distinguish it from other components of the formulation, such as the carrier.

Pharmaceutical compositions of the invention typically contain a therapeutically effective amount of a crystalline compound. Those skilled in the art will recognize, however, that a pharmaceutical composition may contain more than a therapeutically effective amount, i.e., bulk compositions, or less than a therapeutically effective amount, i.e., individual unit doses designed for multiple administration to achieve a therapeutically effective amount. Typically, the composition will contain from about 0.01-95 wt % of active agent, including, from about 0.01-30 wt %, such as from about 0.01-10 wt %, with the actual amount depending upon the formulation itself, the route of administration, the frequency of dosing, and so forth. In one embodiment, a composition suitable for an oral dosage form, for example, may contain about 5-70 wt %, or from about 10-60 wt % of active agent. In one exemplary embodiment, a pharmaceutical composition contains from about 1 to 20 mg of active agent, including from about 1 to 15 mg of active agent and from about 1 to 10 mg of active agent. In another exemplary embodiment, a pharmaceutical composition contains from about 5 to 20 mg of active agent, including from about 7.5 to 15 mg of active agent. For example the active agent may be formulated in 1 mg and 10 mg unit doses.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable composition for a particular mode of administration is well within the scope of those skilled in the pharmaceutical arts. Additionally, carriers or excipients used in such compositions are commercially available. By way of further illustration, conventional formulation techniques are described in *Remington: The Science and Practice of Pharmacy*, 20th Edition, Lippincott Williams & White, Baltimore, Md. (2000); and H. C. Ansel et al., *Pharmaceutical Dosage Forms and Drug Delivery Systems*, 7th Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; compressed propellant gases, such as chlorofluorocarbons and hydrofluorocarbons; and other non-toxic compatible substances employed in pharmaceutical compositions.

Pharmaceutical compositions are typically prepared by thoroughly and intimately mixing or blending the active agent with a pharmaceutically acceptable carrier and one or more optional ingredients. The resulting uniformly blended mixture may then be shaped or loaded into tablets, capsules, pills, canisters, cartridges, dispensers, and the like, using conventional procedures and equipment.

In one embodiment, the pharmaceutical compositions are suitable for oral administration. One exemplary dosing regimen would be an oral dosage form administered once or twice daily. Suitable compositions for oral administration may be in the form of capsules, tablets, pills, lozenges, cachets, dragees, powders, granules; solutions or suspensions in an aqueous or non-aqueous liquid; oil-in-water or water-in-oil liquid emulsions; elixirs or syrups; and the like; each containing a predetermined amount of the active agent.

When intended for oral administration in a solid dosage form (i.e., as capsules, tablets, pills, and the like), the composition will typically comprise the active agent and one or more pharmaceutically acceptable carriers, such as sodium citrate or dicalcium phosphate. Solid dosage forms may also comprise: fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants may also be present in the pharmaceutical compositions. Exemplary coating agents for tablets, capsules, pills and like, include those used for enteric coatings, such as cellulose acetate phthalate, polyvinyl acetate phthalate, hydroxypropyl methylcellulose phthalate, methacrylic acid-methacrylic acid ester copolymers, cellulose acetate trimellitate, carboxymethyl ethyl cellulose, hydroxypropyl methyl cellulose acetate succinate, and the like. Examples of pharmaceutically acceptable antioxidants include: water-soluble antioxidants, such as ascorbic acid, cysteine hydrochloride, sodium bisulfate, sodium metabisulfate, sodium sulfite, and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like.

Compositions may also be formulated to provide slow or controlled release of the active agent using, by way of example, hydroxypropyl methyl cellulose in varying proportions or other polymer matrices, liposomes and/or microspheres. In addition, the pharmaceutical compositions of the invention may contain opacifying agents and may be formulated so that they release the active agent only, or preferentially, in a certain portion of the gastrointestinal tract, optionally, in a delayed manner. Examples of embedding compositions which can be used include polymeric substances and waxes. The active agent can also be in microencapsulated form, if appropriate, with one or more of the above-described excipients.

Suitable liquid dosage forms for oral administration include, by way of illustration, pharmaceutically acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (e.g., cottonseed, groundnut, corn, germ, olive, castor and sesame oils), glycerol, tetrahydrofuryl alcohol, polyethylene glycols and fatty acid esters of sorbitan, and mixtures thereof. Suspensions may contain suspending agents such as, for example, ethoxylated isostearyl alcohols, polyoxyethylene sorbitol and sorbitan esters, microcrystalline cellulose, aluminium metahydroxide, bentonite, agar-agar and tragacanth, and mixtures thereof.

When intended for oral administration, the pharmaceutical compositions of the invention may be packaged in a unit dosage form. The term "unit dosage form" refers to a physically discrete unit suitable for dosing a patient, i.e., each unit containing a predetermined quantity of the active agent calculated to produce the desired therapeutic effect either alone or in combination with one or more additional units. For example, such unit dosage forms may be capsules, tablets, pills, and the like.

In another embodiment, the compositions of the invention are suitable for inhaled administration, and will typically be in the form of an aerosol or a powder. Such compositions are generally administered using well-known delivery devices, such as a nebulizer, dry powder, or metered-dose inhaler. Nebulizer devices produce a stream of high velocity air that causes the composition to spray as a mist that is carried into a patient's respiratory tract. An exemplary nebulizer formulation comprises the active agent dissolved in a carrier to form a solution, or micronized and combined with a carrier to form a suspension of micronized particles of respirable size. Dry powder inhalers administer the active agent as a free-flowing powder that is dispersed in a patient's air-stream during inspiration. An exemplary dry powder formulation comprises the active agent dry-blended with an excipient such as lactose, starch, mannitol, dextrose, polylactic acid, polylactide-co-glycolide, and combinations thereof. Metered-dose inhalers discharge a measured amount of the active agent using compressed propellant gas. An exemplary metered-dose formulation comprises a solution or suspension of the active agent in a liquefied propellant, such as a chlorofluorocarbon or hydrofluoroalkane. Optional components of such formulations include co-solvents, such as ethanol or pentane, and surfactants, such as sorbitan trioleate, oleic acid, lecithin, and glycerin. Such compositions are typically prepared by adding chilled or pressurized hydrofluoroalkane to a suitable container containing the active agent, ethanol (if present) and the surfactant (if present). To prepare a suspension, the active agent is micronized and then combined with the propellant. Alternatively, a suspension formulation can be prepared by spray drying a coating of surfactant on micronized particles of the active agent. The formulation is then loaded into an aerosol canister, which forms a portion of the inhaler.

The crystalline compounds can also be administered parenterally (e.g., by subcutaneous, intravenous, intramuscular, or intraperitoneal injection). For such administration, the active agent is provided in a sterile solution, suspension, or emulsion. Exemplary solvents for preparing such formulations include water, saline, low molecular weight alcohols such as propylene glycol, polyethylene glycol, oils, gelatin, fatty acid esters such as ethyl oleate, and the like. A typical parenteral formulation is a sterile pH 4-7 aqueous solution of the active agent. Parenteral formulations may also contain one or more solubilizers, stabilizers, preservatives, wetting agents, emulsifiers, and dispersing agents. These formulations may be rendered sterile by use of a sterile injectable medium, a sterilizing agent, filtration, irradiation, or heat.

The crystalline compounds can also be administered transdermally using known transdermal delivery systems and excipients. For example, the compound can be admixed with permeation enhancers, such as propylene glycol, polyethylene glycol monolaurate, azacycloalkan-2-ones, and the like, and incorporated into a patch or similar delivery system. Additional excipients including gelling agents, emulsifiers and buffers, may be used in such transdermal compositions if desired.

Secondary Agents

The crystalline compounds may be useful as the sole treatment of a disease or may be combined with one or more other therapeutic agents in order to obtain the desired therapeutic effect. Thus, in one embodiment, pharmaceutical compositions of the invention contain other drugs that are co-administered with a crystalline compound. For example, the composition may further comprise one or more drugs (also referred to as "secondary agents(s)"). Numerous examples of such therapeutic agents are well known in the art, and examples are described herein. By combining a crystalline compound of the invention with a secondary agent, double therapy can be achieved, i.e., serotonin reuptake inhibition activity and activity associated with the secondary agent. Accordingly, in yet another aspect of the invention, a pharmaceutical composition comprises a crystalline compound, a second active agent, and a pharmaceutically acceptable carrier. Third, fourth etc. active agents may also be included in the composition. In combination therapy, the amount of crystalline compound that is administered, as well as the amount of secondary agents, may be less than the amount typically administered in monotherapy.

The crystalline compounds may be either physically mixed with the second active agent to form a composition containing both agents; or each agent may be present in separate and distinct compositions which are administered to the patient simultaneously or sequentially. For example, the crystalline compounds can be combined with a second active agent using conventional procedures and equipment to form a combination of active agents comprising a crystalline compound and a second active agent. Additionally, the active agents may be combined with a pharmaceutically acceptable carrier to form a pharmaceutical composition comprising a crystalline compound, a second active agent, and a pharmaceutically acceptable carrier. In this embodiment, the components of the composition are typically mixed or blended to create a physical mixture. The physical mixture is then administered in a therapeutically effective amount using any of the routes described herein.

Alternatively, the active agents may remain separate and distinct before administration to the patient. In this embodiment, the agents are not physically mixed together before administration but are administered simultaneously or at separate times as separate compositions. Such compositions can be packaged separately or may be packaged together in a kit. When administered at separate times, the secondary agent will typically be administered less than 24 hours after administration of the crystalline compound of the invention, ranging anywhere from concurrent with administration of the crystalline compound to about 24 hours post-dose. This is also referred to as sequential administration. Thus, a crystalline compound can be orally administered simultaneously or sequentially with another active agent using two tablets, with one tablet for each active agent, where sequential may mean being administered immediately after administration of the crystalline compound or at some predetermined time later (e.g., one hour later or three hours later). Alternatively, the combination may be administered by different routes of administration, i.e., one orally and the other by inhalation.

In one embodiment, the kit comprises a first dosage form comprising a crystalline compound and at least one additional dosage form comprising one or more of the secondary agents set forth herein, in quantities sufficient to carry out the methods of the invention. The first dosage form and the second (or third, etc,) dosage form together comprise a therapeutically effective amount of active agents for the treatment or prevention of a disease or medical condition in a patient.

Secondary agent(s), when included, are present in a therapeutically effective amount, i.e., are typically administered in an amount that produces a therapeutically beneficial effect when co-administered with the crystalline compound of the invention. The secondary agent can be in the form of a pharmaceutically acceptable salt, solvate, optically pure stereoisomer, and so forth. Thus, secondary agents listed below are intended to include all such forms, and are commercially available or can be prepared using conventional procedures and reagents.

In one embodiment, a crystalline compound is administered in combination with an α-adrenergic antagonist, representative examples of which include, but are not limited to, doxazosin, prazosin, tamsulosin, and terazosin.

The crystalline compounds may also be administered in combination with $\beta_1$-adrenergic receptor antagonist ("$\beta_1$-blockers"). Representative $\beta_1$-blockers include, but are not limited to, acebutolol, alprenolol, amosulalol, arotinolol, atenolol, befunolol, betaxolol, bevantolol, bisoprolol, bopindolol, bucindolol, bucumolol, bufetolol, bufuralol, bunitrolol, bupranolol, bubridine, butofilolol, carazolol, carteolol, carvedilol, celiprolol, cetamolol, cloranolol, dilevalol, epanolol, esmolol, indenolol, labetolol, levobunolol, mepindolol, metipranolol, metoprolol such as metoprolol succinate and metoprolol tartrate, moprolol, nadolol, nadoxolol, nebivalol, nipradilol, oxprenolol, penbutolol, perbutolol, pindolol, practolol, pronethalol, propranolol, sotalol, sufinalol, talindol, tertatolol, tilisolol, timolol, toliprolol, xibenolol, and combinations thereof In one particular embodiment, the $\beta_1$-antagonist is selected from atenolol, bisoprolol, metoprolol, propranolol, sotalol, and combinations thereof Typically, the $\beta_1$-blocker will be administered in an amount sufficient to provide from about 2-900 mg per dose.

In one embodiment, the crystalline compounds are administered in combination with a $\beta_2$-adrenergic receptor agonist, representative examples of which include, but are not limited to, albuterol, bitolterol, fenoterol, formoterol, indacaterol, isoetharine, levalbuterol, metaproterenol, pirbuterol, salbutamol, salmefamol, salmeterol, terbutaline, and the like. Typically, the $\beta_2$-adrenoreceptor agonist will be administered in an amount sufficient to provide from about 0.05-500 mg per dose.

The crystalline compounds can also be administered in combination with an angiotensin-converting enzyme (ACE) inhibitor. Representative ACE inhibitors include, but are not limited to, accupril, alacepril, benazepril, benazeprilat, captopril, ceranapril, cilazapril, delapril, enalapril, enalaprilat, fosinopril, fosinoprilat, imidapril, lisinopril, moexipril, monopril, moveltopril, pentopril, perindopril, quinapril, quinaprilat, ramipril, ramiprilat, saralasin acetate, spirapril, temocapril, trandolapril, zofenopril, and combinations thereof In a particular embodiment, the ACE inhibitor is selected from: benazepril, enalapril, lisinopril, ramipril, and combinations thereof In one embodiment, the crystalline compounds are administered in combination with an anticoagulant, representative examples of which include, but are not limited to: coumarines such as warfarin; heparin; and direct thrombin inhibitors such as argatroban, bivalirudin, dabigatran, and lepirudin.

In another embodiment, the crystalline compounds are administered in combination with an anti-thrombotic agent. Representative anti-thrombotic agents include, but are not limited to, aspirin, anti-platelet agents, heparin, and combinations thereof Anti-platelet agents include: adenosine diphosphate receptor inhibitors such as clopidogrel (e.g., clopidogrel bisulfate), prasugrel, and ticlopidine; phosphodiesterase inhibitors such as cilostazol; glycoprotein IIB/IIIA inhibitors, typically administered intravenously, such as abciximab, defibrotide, eptifibatide, and tirofiban; and adenosine reuptake inhibitors such as dipyridamole. Exemplary combination anti-thrombotic agents include aspirin combined with dipyridamole.

In one embodiment, the crystalline compounds are administered in combination with a calcium channel blocker. Representative calcium channel blockers include, but are not limited to, amlodipine, anipamil, aranipine, barnidipine, bencyclane, benidipine, bepridil, clentiazem, cilnidipine, cinnarizine, diltiazem, efonidipine, elgodipine, etafenone, felodipine, fendiline, flunarizine, gallopamil, isradipine, lacidipine, lercanidipine, lidoflazine, lomerizine, manidipine, mibefradil, nicardipine, nifedipine, niguldipine, niludipine, nilvadipine, nimodipine, nisoldipine, nitrendipine, nivaldipine, perhexiline, prenylamine, ryosidine, semotiadil, terodiline, tiapamil, verapamil, and combinations thereof In a particular embodiment, the calcium channel blocker is selected from amlodipine, bepridil, diltiazem, felodipine, isradipine, lacidipine, nicardipine, nifedipine, niguldipine, niludipine, nimodipine, nisoldipine, ryosidine, verapamil, and combinations thereof Typically, the calcium channel blocker will be administered in an amount sufficient to provide from about 2-500 mg per dose.

In one embodiment, the crystalline compounds are administered in combination with a diuretic. Representative diuretics include, but are not limited to: carbonic anhydrase inhibitors such as acetazolamide and dichlorphenamide; loop diuretics, which include sulfonamide derivatives such as acetazolamide, ambuside, azosernide, bumetanide, butazolamide, chloraminophenamide, clofenamide, clopamide, clorexolone, disulfamide, ethoxolamide, furosemide, mefruside, methazolamide, piretanide, torsemide, tripamide, and xipamide, as well as non-sulfonamide diuretics such as ethacrynic acid and other phenoxyacetic acid compounds such as tienilic acid, indacrinone and quincarbate; osmotic diuretics such as mannitol; potassium-sparing diuretics, which include aldosterone antagonists such as spironolactone, and $Na^+$ channel inhibitors such as amiloride and triamterene; thiazide and thiazide-like diuretics such as althiazide, bendroflumethiazide, benzylhydrochlorothiazide, benzthiazide, buthiazide, chlorthalidone, chlorothiazide, cyclopenthiazide, cyclothiazide, epithiazide, ethiazide, fenquizone, flumethiazide, hydrochlorothiazide, hydroflumethiazide, indapamide, methylclothiazide, meticrane, metolazone, paraflutizide, polythiazide, quinethazone, teclothiazide, and trichloromethiazide; and combinations thereof In a particular embodiment, the diuretic is selected from amiloride, bumetanide, chlorothiazide, chlorthalidone, dichlorphenamide, ethacrynic acid, furosemide, hydrochlorothiazide, hydroflumethiazide, indapamide, methylclothiazide, metolazone, torsemide, triamterene, and combinations thereof The diuretic will be administered in an amount sufficient to provide from about 5-50 mg per day, more typically 6-25 mg per day, with common dosages being 6.25 mg, 12.5 mg, or 25 mg per day.

In a particular embodiment, the crystalline compound is administered in combination with an endothelin receptor antagonist. Representative endothelin receptor antagonists include, but are not limited to, selective endothelin receptor antagonists (e.g., sitaxentan, ambrisentan, atrasentan, BQ-123), which affect endothelin A receptors, and dual endothelin receptor antagonists (e.g., bosentan, tezosentan), which affect both endothelin A and B receptors.

In another embodiment, the crystalline compounds are administered in combination with a muscarinic antagonist (i.e., anticholinergic agent). Representative muscarinic antagonists include, but are not limited to, atropine, atropine sulfate, atropine oxide, methylatropine nitrate, homatropine hydrobromide, hyoscyamine (d, l) hydrobromide, scopolamine hydrobromide, ipratropium bromide, oxitropium bromide, tiotropium bromide, methantheline, propantheline bromide, anisotropine methyl bromide, clidinium bromide, copyrrolate (Robinul), isopropamide iodide, mepenzolate bromide, tridihexethyl chloride (Pathilone), hexocyclium methylsulfate, cyclopentolate hydrochloride, tropicamide, trihexyphenidyl hydrochloride, pirenzepine, telenzepine, AF-DX 116 and methoctramine and the like.

In still another embodiment, the crystalline compounds are administered in combination with a non-steroidal anti-inflammatory agent (NSAID). Representative non-steroidal anti-inflammatory agents (NSAIDs) include, but are not limited to: acemetacin, acetyl salicylic acid, alclofenac, alminoprofen, amfenac, amiprilose, amoxiprin, anirolac, apazone, aspirin, azapropazone, benorilate, benoxaprofen, bezpiperylon, broperamole, bucloxic acid, carprofen, clidanac, diclofenac, diflunisal, diftalone, enolicam, etodolac, etoricoxib, fenbufen, fenclofenac, fenclozic acid, fenoprofen, fentiazac, feprazone, flufenamic acid, flufenisal, fluprofen, flurbiprofen, furofenac, ibufenac, ibuprofen, indomethacin, indoprofen, isoxepac, isoxicam, ketoprofen, ketorolac, lofemizole, lornoxicam, meclofenamate, meclofenamic acid, mefenamic acid, meloxicam, mesalamine, miroprofen, mofebutazone, nabumetone, naproxen, niflumic acid, nimesulide, nitroflurbiprofen, olsalazine, oxaprozin, oxpinac, oxyphenbutazone, phenylbutazone, piroxicam, pirprofen, pranoprofen, salsalate, sudoxicam, sulfasalazine, sulindac, suprofen, tenoxicam, tiopinac, tiaprofenic acid, tioxaprofen, tolfenamic acid, tolmetin, triflumidate, zidometacin, zomepirac, and combinations thereof. In a particular embodiment, the NSAID is selected from etodolac, flurbiprofen, ibuprofen, indomethacin, ketoprofen, ketorolac, meloxicam, naproxen, oxaprozin, piroxicam, and combinations thereof In a particular embodiment, the crystalline compounds are administered in combination with a phosphodiesterase-5 (PDE-5) inhibitor. Representative PDE-5 inhibitors include, but are not limited to, avanafil, lodenafil, mirodenafil, sildenafil (Revatio®), tadalafil (Adcirca®), vardenafil (Levitra®), and udenafil.

In another embodiment, the crystalline compounds are administered in combination with a prostaglandin analog (also referred to as prostanoids or prostacyclin analogs).

Representative prostaglandin analogs include, but are not limited to, beraprost sodium, bimatoprost, epoprostenol, iloprost, latanoprost, travoprost, and treprostinil.

The following formulations illustrate representative pharmaceutical compositions of the present invention:

Exemplary Hard Gelatin Capsules For Oral Administration

A crystalline compound of the invention (50 g), spray-dried lactose (440 g) and magnesium stearate (10 g) are thoroughly blended. The resulting composition is then loaded into hard gelatin capsules (500 mg of composition per capsule).

Alternately, a crystalline compound (20 mg) is thoroughly blended with starch (89 mg), microcrystalline cellulose (89 mg) and magnesium stearate (2 mg). The mixture is then passed through a No. 45 mesh U.S. sieve and loaded into a hard gelatin capsule (200 mg of composition per capsule).

Exemplary Gelatin Capsule Formulation For Oral Administration

A crystalline compound of the invention (100 mg) is thoroughly blended with polyoxyethylene sorbitan monooleate (50 mg) and starch powder (250 mg). The mixture is then loaded into a gelatin capsule (400 mg of composition per capsule).

Alternately, a crystalline compound (40 mg) is thoroughly blended with microcrystalline cellulose (Avicel PH 103; 259.2 mg) and magnesium stearate (0.8 mg). The mixture is then loaded into a gelatin capsule (Size #1, White, Opaque) (300 mg of composition per capsule).

Exemplary Tablet Formulation For Oral Administration

A crystalline compound of the invention (10 mg), starch (45 mg) and microcrystalline cellulose (35 mg) are passed through a No. 20 mesh U.S. sieve and mixed thoroughly. The granules so produced are dried at 50-60° C. and passed through a No. 16 mesh U.S. sieve. A solution of polyvinylpyrrolidone (4 mg as a 10% solution in sterile water) is mixed with sodium carboxymethyl starch (4.5 mg), magnesium stearate (0.5 mg), and talc (1 mg), and this mixture is then passed through a No. 16 mesh U.S. sieve. The sodium carboxymethyl starch, magnesium stearate and talc are then added to the granules. After mixing, the mixture is compressed on a tablet machine to afford a tablet weighing 100 mg.

Alternately, a crystalline compound (250 mg) is thoroughly blended with microcrystalline cellulose (400 mg), silicon dioxide fumed (10 mg), and stearic acid (5 mg). The mixture is then compressed to form tablets (665 mg of composition per tablet).

Alternately, a crystalline compound (400 mg) is thoroughly blended with cornstarch (50 mg), croscarmellose sodium (25 mg), lactose (120 mg), and magnesium stearate (5 mg). The mixture is then compressed to form a single-scored tablet (600 mg of compositions per tablet).

Exemplary Suspension Formulation For Oral Administration

The following ingredients are mixed to form a suspension containing 100 mg of active agent per 10 mL of suspension:

| Ingredients | Amount |
| --- | --- |
| Crystalline compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum ® K (magnesium aluminum silicate) | 1.0 g |
| Flavoring | 0.035 mL |
| Colorings | 0.5 mg |
| Distilled water | q.s. to 100 mL |

Exemplary Injectable Formulation For Administration By Injection

A crystalline compound of the invention (0.2 g) is blended with 0.4 M sodium acetate buffer solution (2.0 mL). The pH of the resulting solution is adjusted to pH 4 using 0.5 N aqueous hydrochloric acid or 0.5 N aqueous sodium hydroxide, as necessary, and then sufficient water for injection is added to provide a total volume of 20 mL. The mixture is then filtered through a sterile filter (0.22 micron) to provide a sterile solution suitable for administration by injection.

Exemplary Compositions For Administration By Inhalation

A crystalline compound of the invention (0.2 mg) is micronized and then blended with lactose (25 mg). This blended mixture is then loaded into a gelatin inhalation cartridge. The contents of the cartridge are administered using a dry powder inhaler, for example.

Alternately, a micronized crystalline compound (10 g) is dispersed in a solution prepared by dissolving lecithin (0.2 g) in demineralized water (200 mL). The resulting suspension is spray dried and then micronized to form a micronized composition comprising particles having a mean diameter less than about 1.5 pm. The micronized composition is then loaded into metered-dose inhaler cartridges containing pressurized 1,1,1,2-tetrafluoroethane in an amount sufficient to provide about 10 μg to about 500 μg of the compound of the invention per dose when administered by the inhaler.

Alternately, a crystalline compound (25 mg) is dissolved in citrate buffered (pH 5) isotonic saline (125 mL). The mixture is stirred and sonicated until the compound is dissolved. The pH of the solution is checked and adjusted, if necessary, to pH 5 by slowly adding aqueous 1N sodium hydroxide. The solution is administered using a nebulizer device that provides about 10 µg to about 500 µg of the crystalline compound per dose.

EXAMPLES

The following Preparations and Examples are provided to illustrate specific embodiments of the invention. These dihydrate (1.7 g, 4.6 mmol), (DHQ)2Pyr (20 g, 20 mmol, 0.01 eq.), and t-butyl alcohol (6.1 L), were combined in water (6.9 L). The mixture was stirred for 30 minutes, then cooled to 3° C. (R)-3-vinylpyrrolidine-1-carboxylic acid t-butyl ester (460 g, 2.3 mol, 1.0 eq.) in t-butyl alcohol (766.7 mL) was added, and the mixture was allowed to cool at 1° C. The mixture was stirred overnight, and IPC (GC) analysis then indicated that the reaction product was a 2:98 mixture of the SR:SS isomers. The mixture was warmed to 25° C. and water (3 L) was added, yielding a partial slurry. The layers were allowed to separate. The aqueous layer was back extracted with IPAc (4 L), then stirred for 30 minutes at 25 ° C. The aqueous layer was further diluted with water and again back extracted with IPAc (4 L). The layers were separated and the aqueous was removed. The remaining organic layer was combined with the previously separated organic layers, and washed with a saturated aqueous $NH_4Cl$ solution in water (3 L). The layers were separated and the organic layer was concentrated under reduced pressure to afford a thick solution. This solution was taken up with IPAc (1.5 L).

The mixture was seeded with (S)-3-((S)-1,2-dihydroxyethyl)pyrrolidine-1-carboxylic acid t-butyl ester (prepared in a manner as described above) and stirred for 2 hours at room temperature. Crystallization started after few minutes of stirring. The slurry was cooled to 2° C. and stirred at that temperature for 2 days. The slurry was filtered and the resulting cake was washed with IPAc (153 mL) then dried under vacuum to yield the title compound (370 g, purity 99%).

The mother liquor (containing a 2:98 mixture of the SR:SS isomers) was concentrated to yield a thick oil/solid and was taken up in IPAc (307 mL) to form a slurry. This was stirred for 2 hours at room temperature. The slurry was filtered, washed with IPAc (5 mL), and dried to yield an additional 100 g (purity 97%) of the title compound.

Preparation 3

(S)-(S)-3-Oxiranylpyrrolidine-1-carboxylic Acid t-Butyl Ester

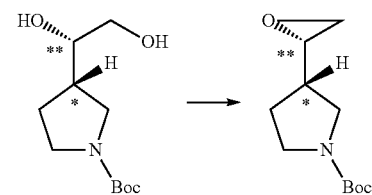 [SMILES: CC(C)(C)OC(=O)N1CC[C@H]([C@H](O)CO)C1 ; CC(C)(C)OC(=O)N1CC[C@H]([C@H]2CO2)C1]

(S)-3-((S)-1,2-Dihydroxyethyl)pyrrolidine-1-carboxylic acid t-butyl ester (230 g, 990 mmol, 1.0 eq.) was combined with MeTHF (4.9 kg, 57 mol) and cooled to 0° C. 2.0 M Sodium t-butoxide in THF (994 mL, 2.0 eq.) was added drop wise over 20 minutes. The mixture was stirred at −1° C. for 15 minutes, then cooled to −7° C. p-Tolylsulfonyl)imidazole (243 g, 1.1 mol, 1.1 eq.) was added and the resulting mixture was stirred at 0° C. for 2 hours. The reaction was quenched with cold $H_2O$ (5.7 kg, 320 mol). Hexanes (1.8 kg, 21 mol) was added and the mixture was warmed to 23° C. and stirred for about 30 minutes. The layers were allowed to settle, the phases were separated, and the reaction vessel was rinsed with MeTHF (100 mL). The organic layer (~8 L) was removed and stored at 5° C. overnight, then filtered through $Na_2SO_4$ and concentrated at 60 torr to 30 torr with a water bath at 25° C. to yield the title compound (220 g).

Example 1

Crystalline Hydrochloride Salt Anhydrous Form I and Anhydrous Form II of (S)-3-VS)-2-Methanesulfonyl-1-(4-trifluoromethylphenoxy)ethyl]pyrrolidine

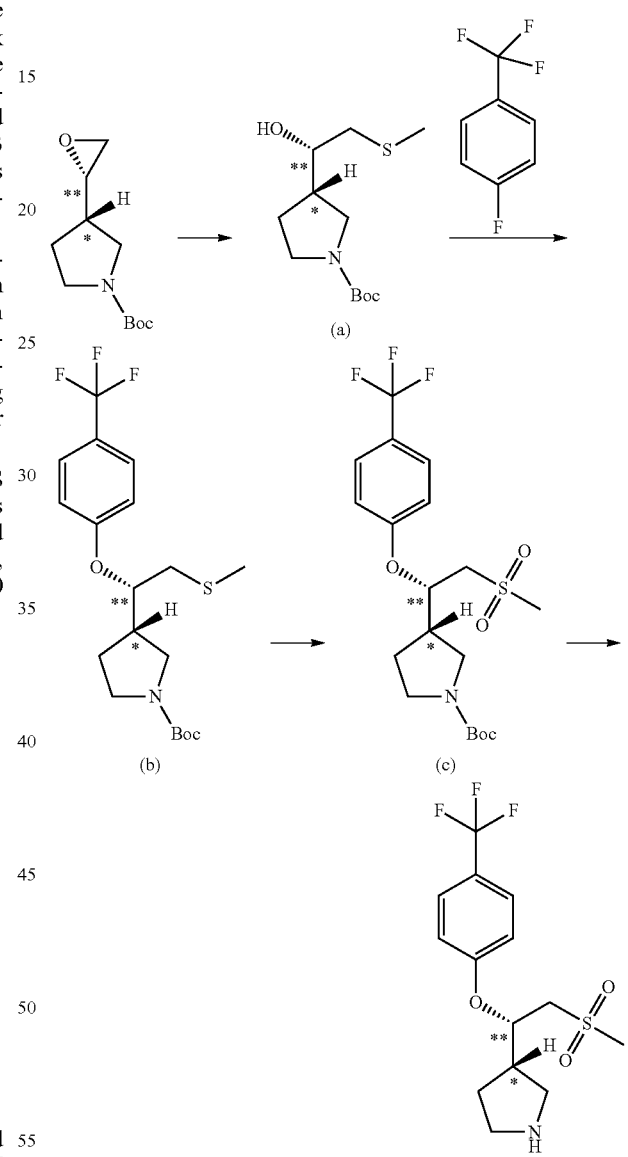

(S)-(S)-3-Oxiranylpyrrolidine-1-carboxylic acid t-butyl ester (440.0 g, 2.0 mol, 1.0 eq.) was combined with DMF (2 L) at 15° C. While stirring, sodium methyl mercaptide (149 g, 2070 mmol, 0.1 eq.) was added in 5 portions over 30 minutes, while maintaining the temperature below 25° C. The mixture was cooled to 18° C., and additional sodium methyl mercaptide (7 g, 100 mmol) was added, and the mixture was stirred for 30 minutes at 25° C. The mixture was cooled to 0° C. and water (10 kg) was added with stirring. IPAc (9 kg, 80 mol) was added, the mixture was warmed to 20° C. and stirred for 30 minutes to allow for phase separation. The aqueous layer was removed and a saturated $NH_4Cl$ solution (0.37:0.63, $NH_4Cl:H_2O$, 5 L) was added to the organic layer. The mixture was stirred for 30 minutes at 25° C., the layers were allowed to separate and the aqueous layer was removed. The organic layer was concentrated by rotary evaporation to yield a yellow oil (430 g). The aqueous layers were maintained at 5° C. for 2 days, warmed to room temperature and back extracted with IPAc (1.2 L). The resulting organic layer was washed with a saturated $NH_4Cl$ solution, the layers were separated, and the organic layer was concentrated under reduced pressure to yield a yellow oil (19 g). The two oil residues were taken up in IPAc (1 L) and concentrated under reduced pressure to yield crude containing compound (a) as a yellow oil (455.0 g) and residual solvents.

DMF (900 g, 10 mol) was added to compound (a) (448.0 g, 1.7 mol, 1.0 eq.) and stirred to obtain a homogeneous solution. The solution was processed in two identical batches of equal amount. Half of the mixture (661 g) was combined with 1-fluoro-4-trifluoromethylbenzene (430.0 g, 2.6 mol, 1.5 eq.) in DMF (2 L). The mixture was cooled to 3° C. followed by the dropwise addition of 2.0 M of sodium t-butoxide in THF (503.0 mL). The mixture was stirred for at least 5 hours, while maintaining the temperature at 4° C. 2 M of Ammonium chloride in water (10 L) was slowly added. The temperature was progressively increased to 25° C. IPAc (7 L) was added and the mixture was stirred for 1 hour, and the phases were allowed to separate. The aqueous layer was removed, leaving the organic layer, which was partially concentrated under reduced pressure then washed with a NaCl solution to yield crude compound (b). The second half of the mixture was then processes similarly and the two crudes were combined to yield crude compound (b).

Crude compound (b) (769.0 g, 1.7 mol, 1.0 eq.) was dissolved in trifluoromethyl benzene (6.5 L) and stirred at 0° C. Ethaneperoxoic acid (1.6 L) was added dropwise, and the resulting mixture was stirred for 1 hour as the temperature was raised to room temperature, then stirred for an additional hour at room temperature. The mixture was cooled to 15° C., followed by a slow quench with water (7 L). The phases were allowed to separate and the organic layer was washed with a 7.5% sodium bicarbonate solution (0.75:9.25, sodium carbonate:$H_2O$, 7 L). The mixture was stirred for 30 minutes at 22° C. and the layers were separated. The organic layer was dried over $Na_2SO_4$ and the solvent was removed by rotary evaporation to yield a thick yellow oil. CPME (2.5 L) was added and mixed at 20° C., followed by addition of heptanes (1.7 L) and previously prepared solid compound (c) (1 g). The mixture was stirred for 1 hour, followed by the slow addition of heptanes (1.6 L). The resulting thick slurry was filtered and the filter cake was washed with hexanes and dried under nitrogen for 2 days to yield compound (c). 3.0 M HCl in CPME (2.0 L) was slowly added to a mixture of compound (c) (318.9 g, 729.0 mmol, 1.0 eq.) and CPME (1.3 L). The resulting mixture was stirred at 20° C. overnight. Additional 3.0 M HCl in CPME (2.0 L) was added and the mixture was again stirred at 20° C. overnight. The reaction vessel was drained and rinsed with CPME (500 mL) and the washes were combined with the slurry. The slurry was filtered and the cake was washed with CPME (200 mL), dried under nitrogen overnight, dried under vacuum for 6 hours at 30° C., and at room temperature for 2 days to yield a HCl crystalline material (239.10 g, purity 99%). This material was then analyzed by powder X-ray diffraction, differential scanning calorimetry, and thermal gravimetric analysis, as described in the examples below, and was designated a crystalline anhydrous hydrochloride salt Form I. This data is presented in FIGS. 1-4.

A portion of the solution (10 mL) was filtered separately and air dried for 3 days to yield a HCl crystalline material (1.3 g, purity 99%). This material was characterized and found to be different from the earlier isolated material, and therefore was designated anhydrous Form II.

The reaction vessel was re-washed with CPME (1.5 L) and $H_2O$ (500 g) to collect the remaining solids. The solution was concentrated to dryness and taken up in CPME (500 mL), concentrated again, taken up in CPME (500 mL) and $H_2$(50 g), and allowed to crystallize overnight). The solids were collected, washed with CPME (50 mL) and dried under nitrogen overnight to yield additional crystalline material (20.1 g, purity 99%). This material was then analyzed by powder X-ray diffraction, differential scanning calorimetry, and thermal gravimetric analysis, as described in the examples below, and was designated a crystalline anhydrous hydrochloride salt Form II. This data is presented in FIGS. 6, 8, and 9.

Example 2

Conversion of Crystalline Anhydrous Hydrochloride Salt Form I to Form II

Equal amounts (~50 mg) of anhydrous Form I and anhydrous Form II were weighed out and physically mixed in a vial with a spatula. A solution of MTBE:water (95:5) was added to this solid mixture and stirred to form a suspension. The suspension was stirred at room temperature for three days and filtered through a filter paper. The solid residue was allowed to dry under ambient conditions and analyzed with powder X-ray diffractometry and DSC. The PXRD pattern revealed that the filtered solid contained predominantly (>95%) anhydrous Form II, indicating that anhydrous Form I has converted to anhydrous Form II under these slurry conditions.

Example 3

Recrystallization of Crystalline Anhydrous Hydrochloride Salt Form II

Anhydrous Form II (19 g, 51 mmol) was dissolved in isopropyl alcohol (200 mL, 3000 mmol), and the resulting mixture was heated to 44° C. while stirring. When the light slurry turned into a thick paste that resisted stirring, water (4 mL, 200 mmol) was added and the resulting mixture was heated to 60° C., yielding a yellow solution with some residual insoluble material. The mixture was heated further to 70° C. and hot filtered through a pre-heated filter. The mixture was allowed to cool down and isopropyl alcohol (50 mL, 600 mmol) was added, followed by seeding with anhydrous Form II crystals. The crystallization occurred rapidly to form a thick paste that turned to a stirrable slurry over time. After 5 hours, the solids were collected on a pressure filter, washed with isopropyl alcohol and dried overnight under nitrogen. The solids were collected to yield a white solid (14.5 g) with very low bulk density.

This material was then analyzed by powder X-ray diffraction and differential scanning calorimetry, as described in the examples below. This solid form data was found to be consistent with that of the crystalline anhydrous hydrochloride salt Form II. FIG. 7 shows the overlay of the PXRD patterns of the starting material and the product.

Example 4

Crystalline Hydrochloride Salt of (S)-3-[(S)-2-Methanesulfonyl-1-(4-trifluoromethylphenoxy)ethyl]pyrrolidine Monohydrate Solid particles of the anhydrous Form I were exposed to 75% RH for one day. The resulting material was characterized and was found to be a monohydrate. This material was then analyzed by powder X-ray diffraction, differential scanning calorimetry, and thermal gravimetric analysis, as described in the examples below. This data is presented in FIGS. 12, 13, and 14.

Example 5

Powder X-Ray Diffraction

Powder X-ray diffraction analysis of the solids was performed using the Thermo ARL X'Tra X-ray diffractometer. The X-ray source was Cu-Kα radiation (λ=1.54051 Å) with output voltage of 45 kV and current of 40 mA. The instrument was operated in Bragg-Brentano geometry with incident, divergence, and scattering slits set to maximize the intensity at the sample. For measurement, a small amount of powder (5-25 mg) was gently pressed onto a sample holder to form a smooth surface and subjected to X-ray exposure. The samples were scanned in 2θ-2θ mode from 2° to 40° in 2θ with a step size of 0.03° and a scan speed of 2.0° per minute. The data acquisition was controlled by Thermo ARL measurement software (Version 1.2.0.0) and analyzed by Jade software (version 7.5.1). The instrument was calibrated with a quartz standard, within ±0.02° 2θ angle.

It should be kept in mind that the Bragg-Brentano geometry used in the data collection is prone to preferred orientation. Under these conditions it is possible that the relative intensities of the diffraction peaks may not represent the true relative intensities that would be obtained from an idealized distribution of spherical particles or from a diffraction pattern simulated from a single crystal data. It is also possible that some peaks are not seen in some diffraction patterns due to the extensive preferred orientation.

Thermal Analysis

Differential scanning calorimetry (DSC) measurements were performed using a TA Instruments Model Q-100 module with a Thermal Advantage controller. Data were collected and analyzed using TA Instruments Universal Analysis software. A sample of each crystalline form was accurately weighed into a covered aluminum pan. After a 5 minute isothermal equilibration period at 5° C., the sample was heated using a linear heating ramp of 10° C./min from 0° C. to 200° C.

Thermogravimetric analysis (TGA) measurements were performed using a TA Instruments Model Q-50 module equipped with high resolution capability. Data were collected using TA Instruments Thermal Advantage controller and analyzed using TA Instruments Universal Analysis software. A weighed sample was placed onto a platinum pan and scanned with a heating rate of 10° C. from ambient temperature to 200° C. The balance and furnace chambers were purged with nitrogen flow during use.

Dynamic Moisture Sorption Assessment

Dynamic moisture sorption (DMS) measurements were performed for each crystalline form using a VTI atmospheric microbalance, SGA-100 system (VTI Corp., Hialeah, Fla. 33016). A weighed sample was used and the humidity was set at the ambient value at the start of the analysis. The DMS analysis consisted of a scan rate of 5% RH/step over the full humidity range of 5% relative humidity (RH) to 90% RH. The DMS run was performed isothermally at 25° C.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statutes and regulations, all publications, patents, and patent applications cited herein are hereby incorporated by reference in their entirety to the same extent as if each document had been individually incorporated by reference herein.

What is claimed is:

1. A crystalline hydrochloride salt of (S)-3-[(S)-2-methanesulfonyl-1-(4-trifluoromethylphenoxy)ethyl]pyrrolidine; wherein the crystalline hydrochloride salt is selected from: (a) an anhydrous Form I, characterized by a powder x-ray diffraction pattern comprising diffraction peaks at 2θ values of 5.37±0.20, 9.89±0.20, 10.28±0.20, 16.06±0.20, 16.66±0.20, 19.90±0.20, 21.46±0.20, 23.18±0.20, 26.88±0.20, and 27.28±0.20; (b) an anhydrous Form II, characterized by a powder x-ray diffraction pattern comprising diffraction peaks at 2θ values of 7.14±0.20, 9.86±0.20, 11.38±0.20, 14.20±0.20, 15.64±0.20, 18.00±0.20, 21.38±0.20, 22.24±0.20, 30.20±0.20, and 36.36±0.20; and (c) a monohydrate, characterized by a powder x-ray diffraction pattern comprising diffraction peaks at 2θ values of 11.54±0.20, 14.38±0.20, 14.96±0.20, 16.44±0.20, 18.30±0.20, 19.62±0.20, 21.56±0.20, 24.56±0.20, 25.06±0.20, 25.96±0.20, and 26.92±0.20.

2. A pharmaceutical composition comprising a pharmaceutically acceptable carrier and the crystalline hydrochloride salt of claim 1.

3. The pharmaceutical composition of claim 2, further comprising a therapeutic agent selected from calcium channel blockers, endothelin receptor antagonists, PDE-5 inhibitors, prostacycline analogues, prostanoids, and combinations thereof.

* * * * *